US005640967A

United States Patent [19]

Fine et al.

[11] Patent Number: 5,640,967
[45] Date of Patent: Jun. 24, 1997

[54] MONITORING SYSTEM AND METHOD FOR USE DURING AN ELECTROPHYSIOLOGY STUDY

[75] Inventors: Ian Michael Fine, Toronto; Peter Leigh Bartlett, Acton; Harold Max Wodlinger, Thornhill; Randy Au Coin, Scarborough, all of Canada

[73] Assignee: Quinton Electrophysiology Corporation, Richmond Hill, Canada

[21] Appl. No.: 405,065

[22] Filed: Mar. 16, 1995

Related U.S. Application Data

[63] Continuation-in-part of Ser. No. 219,692, Mar. 29, 1994, Pat. No. 5,566,096.

[51] Int. Cl.$^6$ .................................................. A61B 5/044
[52] U.S. Cl. ........................................................... 128/710
[58] Field of Search .............................. 128/696, 709, 128/710, 712

[56] References Cited

U.S. PATENT DOCUMENTS

| | | | |
|---|---|---|---|
| 4,161,945 | 7/1979 | Grossman | 128/696 |
| 4,201,224 | 5/1980 | John | 128/731 |
| 4,249,538 | 2/1981 | Musha et al. | 128/630 |
| 4,331,962 | 5/1982 | Neumann | 128/712 |
| 4,367,753 | 1/1983 | Jirak | 128/708 |
| 4,416,288 | 11/1983 | Freeman | 128/731 |
| 4,417,306 | 11/1983 | Citron et al. | 364/415 |
| 4,513,752 | 4/1985 | Weyant | 128/696 |
| 4,550,370 | 10/1985 | Baker | 364/413 |
| 4,641,649 | 2/1987 | Walinsky et al. | 128/303.1 |
| 4,677,986 | 7/1987 | Decote, Jr. | 128/697 |
| 4,686,988 | 8/1987 | Sholder | 128/419 |
| 4,705,043 | 11/1987 | Imran | 128/419 |
| 4,794,532 | 12/1988 | Leckband et al. | 128/709 |
| 4,979,510 | 12/1990 | Franz et al. | 128/642 |
| 5,016,631 | 5/1991 | Hogrefe | 128/419 |
| 5,018,523 | 5/1991 | Bach, Jr. et al. | 128/419 |
| 5,058,599 | 10/1991 | Andersen | 128/705 |
| 5,086,778 | 2/1992 | Mueller et al. | 128/696 |
| 5,101,832 | 4/1992 | Pritchard et al. | 128/696 |
| 5,239,996 | 8/1993 | Lister et al. | 128/709 |
| 5,262,944 | 11/1993 | Weisner et al. | 128/712 |
| 5,265,616 | 11/1993 | Hoshino | 128/709 |
| 5,365,936 | 11/1994 | Kyu | 128/710 |

OTHER PUBLICATIONS

Bloom Associates, Ltd.; Model BPA Cardiovascular Pressure Amplifier; one page; (no date).
Gould Electronics; Gould: Where Innovation Is a Practical Art; 8 pages (no date).
Bloom Associates, Ltd.; Total Cardiac Electrophysiology System; 6 pages; (no date).
Arrhythmia Research Technology, Inc.; Cardiolab™—Specifications; 3 pages (no date).
Bloom Associates, Ltd; BERS–400A EP Recording Amplifiers and Input Switching System; 3 pages; (no date).

*Primary Examiner*—William E. Kamm
*Attorney, Agent, or Firm*—Montgomery W. Smith; Richard D. Allison

[57] ABSTRACT

A versatile electrophysiology study monitoring system including an amplification system, a real time display monitor and a chart recorder as well as an optional data management and analysis system wherein the display monitor and chart recorder are controllable directly from the amplification system which may be positioned at the bedside of the patient to provide a portable system which may be used at the bedside of the patient or in the electrophysiology laboratory and which also includes a 32 channel display of physiological data and user settable filter settings for high and low pass filters.

17 Claims, 36 Drawing Sheets

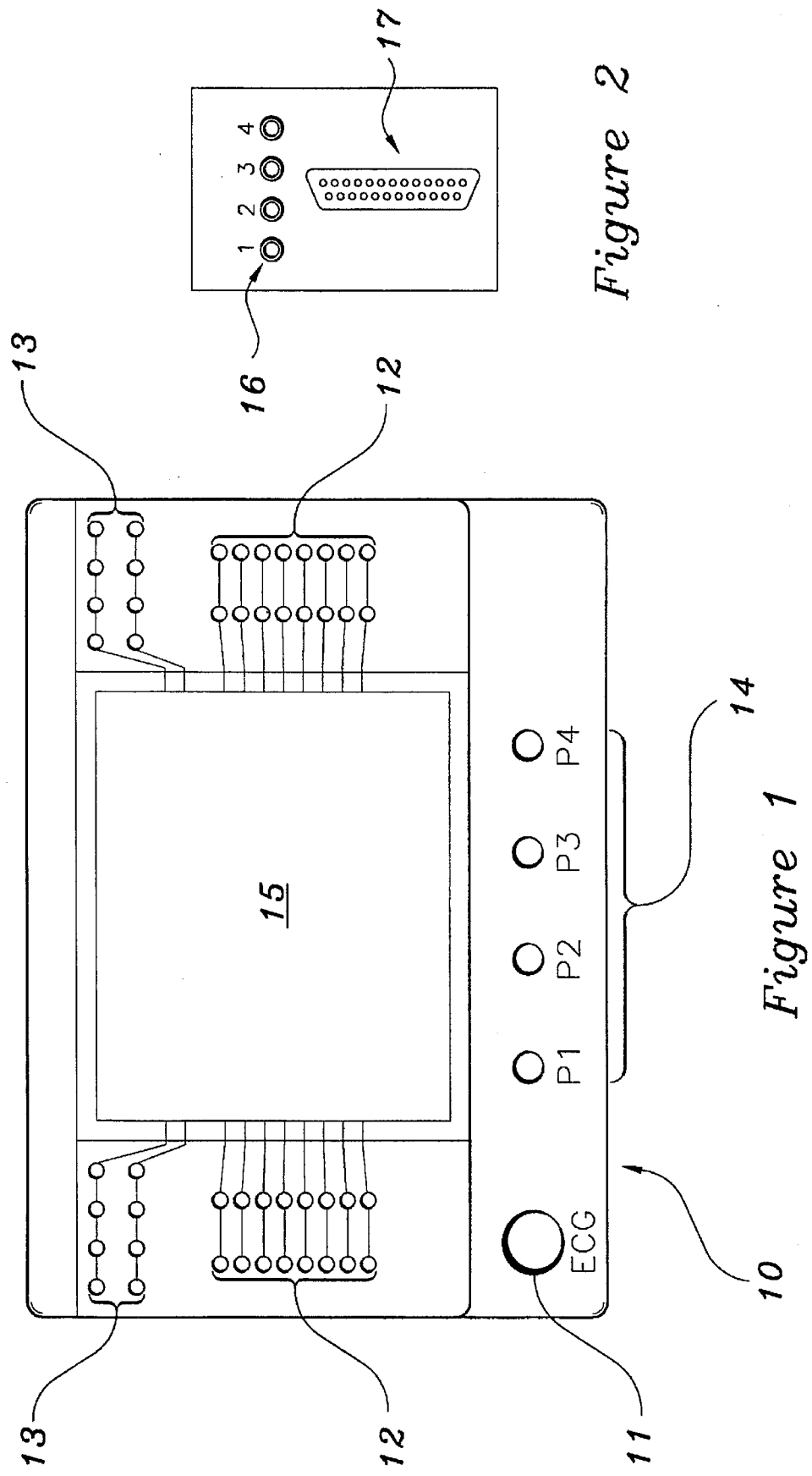

Figure 5(b)

| CHANNELS | LEADS | GAIN | FILTER | LIMITER | NAME |
|---|---|---|---|---|---|
| 1 | | | | | |
| 2 | 1' | 2' | 3' | 4' | 5' | 6' | 7' | 8' | 9' | 0' | aVf |
| 3 | Q | W | E | R | T | Y | U | I | O | P | V6 |
| 4 | A | S | D | F | G | H | J | K | L | : | HRA1-WCT |
| 5 | Z | X | C | V | B | N | M | , | . | + | |
| 6 | | | | DONE | | ▼ | |
| 7 | | | | | | |
| 8 | | | | | | |
| 9 | | | | | | |
| 10 | CS 3-4 | 500 | 30-400 OFF | 500 | CS 3-4 |
| 11 | | | | | | |
| 12 | | | | | | |

Figure 5(e)

| CHANNELS | LEADS | GAIN | FILTER | LIMITER | NAME |
|---|---|---|---|---|---|
| 1 | I | 1 | 13 | 25 | |
| 2 | aVf | 2 aVf | 14 | 26 | |
| 3 | V6 | 3 V6 | 15 | 27 | |
| 4 | HRA1-WCT | 4 HRA1-W | 16 | 28 | |
| 5 | | 5 | 17 | 29 | |
| 6 | | 6 | 18 | 30 | |
| 7 | | 7 | 19 | 31 | |
| 8 | | 8 | 20 | 31 | |
| 9 | | 9 | 21 | | |
| 10 | CS 3-4 | 10 | 22 | | |
| 11 | | 11 | 23 | | |
| 12 | | 12 | 24 | | DELETE |

MAIN

Figure 5(f)

| CHANNELS | LEADS | GAIN | FILTER | LIMITER | NAME |
|---|---|---|---|---|---|
| 1 | I | 1000 | 0.05-100 OFF | 1.5 | I |
| 2 | aVf | 1000 | 0.05-100 OFF | 3.1 | aVf |
| 3 | V6 | 1000 | 0.05-100 OFF | OFF | V6 |
| 4 | HRA1-WCT | 250 | 0.05-400 OFF | OFF | HRA1-WCT |
| 5 | CS 3-4 | 500 | 30-400 OFF | OFF | CS 3-4 |
| 6 | CS 1-2 | 500 | 30-400 OFF | OFF | CS 1-2 |
| 7 | CS 1-4 | 500 | 30-400 OFF | OFF | CS 1-4 |
| 8 | VOLTS | 100 | DC-100 OFF | OFF | VOLTS |
| 9 | CURRNT | 100 | DC-100 OFF | OFF | CURRNT |
| 10 | AORTA | 300 | DC-40 OFF | OFF | AORTA |
| 11 | | | | | |
| 12 | | | | | |

MAIN

*Figure 5(g)*

DISPLAY MENU OPTION

| 12 LEAD | SIGNALS | 12 LEAD | DISPLAY | RESTORE |
|---|---|---|---|---|
| | | INTRACARDIAC | | |
| | | CONFIGURE | | |
| | | TR. SW. SETUP | | |
| | | TR. SW. SW. SCRL | | |
| | | SENSE 1 2 | | |
| | | SPEED | | |
| | | FULL H V | | |
| | | GRID | | |
| | | MAP TAG | | |
| | | CHART | | |
| | | STORE | | |
| | | AUXILIARY | | |
| | | PRESSURE | | |

DISPLAY MONITOR OPTIONS

MAIN MENU

ONE OPTION ON LINE ALWAYS HIGHLIGHTED

*Figure 11*

| 12 LEAD | SIGNALS | 12 LEAD | DISPLAY | RESTORE |
|---|---|---|---|---|
| | | INTRACARDIAC | | |
| | | CONFIGURE | | |
| | | SETUP | | |
| | | TR. SW. SW. SCRL | | |
| | | SENSE 1 2 | | |
| | | SPEED | | |
| | | DISPLAY | | |
| | | 25 25 | | |
| | | 50 50 | | |
| | | 75 75 | | |
| | | 100 100 | | |
| | | 200 200 | | |
| | | 400 400 | | |
| | | DONE | | |

*Figure 12A*

| 12 LEAD | SIGNALS | 12 LEAD | DISPLAY | RESTORE |
|---|---|---|---|---|
| | | INTRACARDIAC | | |
| | | CONFIGURE | | |
| | | NOTCH | | |
| | | 50    60 | | |
| | | AUTO RESTORE | | |
| | | ON    OFF | | |
| | | CALIBRATION | | |
| | | 1 mV   0.1 | | |
| | | DIAGNOSTICS | | |
| | | SYSTEM SETUP | | |
| | | DONE | | |
| | | | | |
| | | AUXILIARY | | |
| | | PRESSURE | | |

*Figure 12B*

| 12 LEAD | SIGNALS | 12 LEAD | DISPLAY | RESTORE |
|---|---|---|---|---|
| | | INTRACARDIAC | | |
| | | CONFIGURE | | |
| | | TR. TR. SETUP | | |
| Ref. Line | Channel | 11 V5 | | 22 |
| Adjustment | 1 I | 12 V6 | | 23 |
| ← → | 2 II | 13 | | 24 |
| | 3 III | 14 | | 25 |
| | 4 aVr | 15 | | 26 |
| Draw Mode | 5 aVl | 16 | | 27 |
| Erase | 6 aVl | 17 | | 28 |
| Overlay | 7 V1 | 18 | | 29 |
| | 8 V2 | 19 | | 30 |
| | 9 V3 | 20 | | 31 |
| Done | 10 V4 | 21 | | Stim |

| 12 LEAD | CATHETERS | 12 LEAD | | DISPLAY | RESTORE |
|---|---|---|---|---|---|
| GAIN | LEADS | GAIN | FILTER | LIMITER | NAME |
| 1 | I | 1 | ECG/IC(mV/cm) | | |
| 2 | II | 1 | 20 | 10 | 5 |
| 3 | III | 1 | 2.5 | 1 | 0.05 |
| 4 | aVr | 1 | 0.25 | 0.1 | 0.05 |
| 5 | aVl | 1 | | | |
| 6 | aVf | 1 | Auxiliary (mV/cm) | | |
| 7 | V1 | 1 | 1000 | 500 | 100 |
| 8 | V2 | 1 | 50 | 10 | 5 |
| 9 | V3 | 1 | | | |
| 10 | V4 | 1 | PRESSURE (mmHG) | | |
| 11 | V5 | 1 | 30 | 150 | 300 |
| 12 | V6 | 1 | DONE | | |

*Figure 12F*

| 12 LEAD | CATHETERS | 12LAD.HRA | SIGNALS | RESTORE |
|---|---|---|---|---|
| CHANNEL | LEADS | GAIN | FILTER | LIMITER | NAME |
| 1 | I | 1 | 0.5-100 | HIGH | LOW |
| 2 | aVf | 1 | 0.5-100 | 12 | |
| 3 | V6 | 1 | 1 2 3 | DC | 20 |
| 4 | HRA1-WCT | 2.5 | 4 5 6 | 0.05 | 40 |
| 5 | CS3-4 | 5 | 7 8 9 | 0.5 | 100 |
| 6 | CS1-2 | 1 | 0 | 1 | 200 |
| 7 | CS1-4 | 1 | DONE | 10 | 400 |
| 8 | VOLTS | 1 | CANCEL | 30 | |
| 9 | CURRNT | 1 | DC-40 | NOTCH | |
| 10 | AORTA | 1 | DC-100 | ON | OFF |
| 11 | III | 1 | 0.5-100 | DONE | |
| 12 | | | | | |

*FILTER VALUE*

*USER DEFINABLE*

*PRESET FILTER VALUES*

*NOTCH ON/OFF*

*USER DEFINABLE FILTER VALUES*

*Figure 12G*

| 12 LEAD | CATHETERS | 12LAD.HRA | SIGNALS | RESTORE |
|---|---|---|---|---|
| | | CHANNEL | NAME | TRACE | COLOR |
| | | ← 1 | I | 1.5 | YELLOW |
| | | 2 | aVf | 3.1 | YELLOW |
| | | 3 | V6 | OFF | YELLOW |
| | | 4 | HRA1-2 | OFF | YELLOW |
| | | 5 | CS3-4 | OFF | YELLOW |
| | | 6 | CS1-2 | OFF | YELLOW |
| | | 7 | CS5-6 | OFF | YELLOW |
| | | 8 | TEMP | OFF | YELLOW |
| | | 9 | NIBP | OFF | YELLOW |
| | | 10 | AORTA | OFF | YELLOW |
| | | 11 | III | OFF | YELLOW |
| | | → 12 | II | OFF | YELLOW |
| ← | + 5.0% − | → |

*Figure 12H*

MONITORING SYSTEM AND METHOD FOR USE DURING AN ELECTROPHYSIOLOGY STUDY

BACKGROUND OF THE INVENTION

The present application is a continuation-in-part of U.S. Ser. No. 08/219,692 filed on Mar. 29, 1994, now U.S. Pat. No. 5,566,096 entitled "Integrated Electrical Signal Switching and Amplifying System," both of which are owned by a common assignee, Quinton Electrophysiology Corp.

FIELD OF THE INVENTION

This invention relates generally to an electrical signal management system. More specifically, the present invention relates to an integrated system for electrical signal switching and amplifying. Also, the present invention relates to an automatic calibration system for calibrating the electrical signal switching and amplifying hardware in the integrated system including a versatile electrophysiology system having a data management and analysis system, a switching and amplification system, a real time display monitor and a chart recorder.

PRIOR ART

In order to more fully appreciate the present invention, it is important to understand the basic principles of Electrophysiology. The electrophysiology study is used to assist in evaluating a broad spectrum of cardiac arrhythmias. The basic electrophysiology procedure involves the recording and pacing of electrical signals within localized areas of the heart. Because the electrophysiology study involves the monitoring of electrical signals in the heart of the patient, the basic unit of time is milliseconds. The heart rate of the patient is referred to in terms of the cycle length which refers to the length of time between each heart beat. Therefore, as the heart rate of the patient increases, the cycle length of the patient decreases. A coupling interval is referred to as the time between the last normal impulse and a premature impulse which may have been stimulated by an internal or external pacemaker. The catheters used in electrophysiology studies consist of insulated wires having a distal end with electrodes thereon which are exposed to the intracardiac surface of the patient. The proximal end of the catheter includes various plugs or connectors thereon which correspond to certain electrodes at the distal end of the catheter.

The recording of the electrical activity from an electrode catheter placed in the heart of the patient is referred to as an intracardiac electrogram. The primary difference between a body surface ECG and an intracardiac electrogram is that the ECG represents a summation of the entire electrical activity of the heart of the patient while the intracardiac electrogram represents the electrical activity of a localized area of interest. One common use of the electrode catheter is to pace the heart of the patient such that premature heart beat is created. Current electrophysiology systems typically perform two types of programmed stimulation. The first type of programmed stimulation is known as incremental or burst pacing where a train of fixed pulses is produced at a fixed cycle length. This type of pacing may last for a few beats or for several minutes. The other primary type of pacing is known as extra-stimulus pacing where one or more premature impulses are produced at their own specific coupling interval. The electrophysiology study allows the physician to move the distal end of the electrode catheter to various locations in the heart of the patient and also to select various electrode pairs to monitor the electrical conduction characteristics of very specific areas of the heart of the patient.

The basic equipment required for an electrophysiology study consists of a programmable stimulator, a multichannel lead switching box, one or more display monitors, a printer and electrode catheters. The programmable stimulator is a specialized pacing unit built particularly for electrophysiology studies. The stimulator has the capability to introduce complex sequences of paced beats to within an accuracy of one millisecond and may also provide pacing which is synchronous with the intrinsic heart rhythm of the patient or perform simultaneous pacing of multiple intracardiac sites.

The multichannel lead switching box or junction box allows the laboratory personnel to control the connections from the electrode catheters to various recording and pacing devices. The switching box includes multiple switches to allow for the sorting of multiple electrode pairs from multiple catheters for recording and pacing the intracardiac areas of interest.

The present invention is directed to a versatile electrophysiology system including a signal amplification system which commonly includes a switch box generally located at a patient's bedside during an electrophysiology procedure. The switch box receives the proximal ends of intracardiac catheter leads, ECG leads, blood pressure sensor leads, breathing sensor leads, temperature sensor leads, pulse sensor leads, or the like. The leads are input by attaching them to input terminals which are arranged on the switch box in a grid-type fashion and labelled for identification either numerically or by color. The switch box outputs to an amplifier which in turn outputs to a computer processing unit, which also in turn output to a monitor or chart recorder if desired.

During setup of the switch box, the computer processing unit must receive information identifying the input locations of each of the leads in the input terminal grid. This is commonly accomplished by having one operator at the patient's bedside attach the leads in one-by-one fashion into the switch box, and then announce to a second operator the identification of each input terminal label corresponding to the particular lead being inserted. The second operator then simultaneously inputs into the computer processing unit the label indicating the particular parameter being monitored and the corresponding output terminal identification number or color as it is announced by the first operator.

After the leads have been attached to the switch box and the computer processing unit has received the necessary labels related to the positioning or colors to which the leads correspond, the procedure is commenced. However, very often during an electrophysiology procedure, it is desirable to either move a catheter to a different position in the patient's heart, to add a catheter, or to compare signals received from various catheters. In any of these events, it is necessary to re-identify the particular label given to the catheter lead so that the changes or additions may be properly input into the computer processing unit. Because of the physical separation of the switch box and the computer processing unit, and the necessity of having two operators perform redundant operations to ensure that the computer processing unit correctly correlates the label of the catheter lead with its position in the switch box, necessary changes during a procedure can cause errors in the analysis data to occur, as well as potential injury to the patient.

Attempts have been made to solve the problem of input terminal/lead label correspondence during setup and operational use of signal acquisition and processing systems such as the electrical signal management system of the present invention, with varying success. For example, U.S. Pat. No.

4,037,586 to Grichnick, describes an electroencephalograph which includes a visual display for indicating the particular pattern in which electrodes connected to the patient are processed to provided desired output signals. Although this invention may help an operator view the particular processing order of signals received by the device, it nevertheless fails to assist the physician in setup of the device for operation or in changing the setup during a procedure.

U.S. Pat. No. 4,695,955 issue to Faisandier, describes a prior art electronic device which acquires and processes signals originating from sensors attached to a patient. The device automatically recognizes a sensor lead attached to an input terminal thereof for the proper signal amplification, energization, and processing elements. This device simplifies setup of a procedure by automatically recognizing the particular lead attached to the input terminal. It nevertheless contains the drawback of requiring the use of leads which can be mechanically identified by the device to initiate automatic programming of the processing system. Further, the device fails to allow relabelling of a lead depending on a change in the corresponding sensors position on the patient, and/or a change in the particular parameter being monitored by the sensor.

OBJECTS AND SUMMARY OF THE INVENTION

An object of the present invention is to provide a versatile electrophysiology system including a complete electrophysiology system consisting of a data management and analysis system, a real time display monitor, an electrical signal switching and amplification system, an interface unit and a chart recorder; or a modified system consisting of a mobile electrical signal switching and amplification system, a real time display monitor and a chart recorder.

It is a further object of the present invention to provide an electrophysiology system having a redundancy which includes an integrated electrical signal switching and amplification system which may function totally independent of any data processing device which may be attached thereto or where the data processing device may operate independently of the real time display monitor and chart recorder so that if one of the systems malfunctions or is somehow disconnected, the procedure may be allowed to continue.

It is also an object of the present invention to provide an a complete 32 channel electrophysiology system which may be controlled by a bedside integrated electrical signal switching and amplifying system with a real time display monitor and chart recorder.

Another object of the present invention is to provide an electrical signal management system which considerably simplifies preprocedure calibration and setup, and also simplifies setup changes during an ongoing signal acquisition and processing procedure.

Another object of the present invention to provide an interactive display screen and software for simplifying setup and operation of the integrated electrical signal switching and amplifying system.

A further object of the present invention to provide the integrated electrical signal switching and amplifying system having an inboard microprocessing capability which allows for the total independent functioning thereof independently of any outside computer processing unit and which also allows storage of predetermined setup configurations for simplification of the setup procedure.

A further object of the present invention to provide the integrated electrical signal switching and amplifying system having user settable filters thereon.

A further object of the present invention is to provide an integrated electrical signal switching and amplifying system which can be completely and independently setup and controlled by an operator at the patient's bedside without the necessity of a second operator recording input terminal identification numbers or colors to an attached computer processing unit as a manner of identifying the output terminal positions of sensor leads.

A further object of the present invention to include a real time display monitor that allows the user to select either panning or scrolling mode of display of 32 channels of data across the monitor and the operation of which may be controlled from the bedside by an integrated electrical signal switching and amplifying system.

Yet another object of the present invention is to provide an electrophysiology system having a real time monitor which is controlled by either or both of the integrated electrical signal switching and amplifying system or a data management system which performs storage, analysis and reporting of the results of the electrophysiology study.

Yet another object of the present invention is to provide a real time monitor having a triggered sweep mode which overlays the data on the digital real time monitor.

These and other objects of the present invention are realized in a presently preferred embodiment therefor, disclosed by way of example and not by way of limitation, which includes an electrophysiology system having an integrated electrical signal switching and amplifying system for use in electrophysiology procedures as an interface between electrical signals received from a patient through sensors such as intracardiac catheters, ECG leads, pressure sensors or the like, and a real time display monitor, chart recorder, or computer processing and analysis unit. The switching and amplification system uses digital technology to amplify and condition electrical signals from a patient's heart and download analog formatted signals to a computer processing unit or a real time display monitor or chart recorder.

The analog output of the amplification system of the present invention has a unique safety advantage over prior art electrophysiology amplification systems in that it ensures the possibility of uninterrupted electrophysiology studies in the event that either the computer processing unit or the real time display or chart recorder fail during the electrophysiology procedure. For example, a chart recorder and/or the real time display monitor could be used alone with the present invention, or in conjunction with a computer processing unit, to record the electrophysiology procedure and chart recorder will continue to print and the real time display monitor will continue to display the wave forms during the procedure. This feature allows the system of the present invention to be used to provide information from an electrophysiology procedure entirely independent from the operation of a computer processing unit or real time display monitor and/or chart recorder if desired or necessary.

The amplification system of the present invention includes a front panel having an interactive display which eliminates potentially confusing cross connections and allows simplified selection and assignment of intracardiac catheters and other sensors during the setup procedure. The amplification system of the present invention also allows catheters or other sensors to be assigned at the patient's bedside by a single operator, and automatically transfers the necessary information to a computer processing unit should it be attached. This eliminates the formerly necessary exchange of information to a separate computer processing unit. This eliminates the formerly necessary exchange of information between an attending physician at the patient's bedside and a separate medical technologist positioned at the computer processing unit.

The amplification system of the present invention also includes a novel electrical hardware design which improves signal conditioning performance and reduces the systems overall physical size. Specifically, the present invention includes at least one digital signal processor (DSP) for comparing signals received from the input terminals thereof, in lieu of prior art systems which include much more bulky analog switching arrays to accomplish this task.

Further, the amplification system of the present invention includes an automatic calibration system which allows the DSP to perform an automated calibration for correction of any variances in performance of the amplifier components and to ensure proper DSP output.

The amplification system of the present invention can also be adapted for use in hemodynamic studies in conjunction with electrophysiology studies due to its ability to receive and process pressure inputs.

The data management and analysis system of the present invention provides up to 32 channels of real time analog wave form acquisition, scrolling or panning displays, storage and statistics. Once storage has been conducted, playback, markers, annotations, analysis and hard copy printouts may be performed. The major components of the data management and analysis system include a micro computer, keyboard, mouse, laser printer and may be interconnected with a separate fluoroscopic viewing system to provide the physician with a means for visually identifying the location of the catheters.

The real time display monitor of the present invention is a real time display system designed to operate with the amplification system at the bedside of the patient. The real time display monitor also preferably includes a quick disconnect system to allow the monitor to be quickly attached to or removed from the data management system and used in a variety of configurations.

In one configuration of electrophysiology system of the present invention an interface unit optionally allows for the interface between the RS-232 serial communication from a data management and analysis system and the RS-485 serial communication of the real time display monitor. Additionally, the interface unit includes a multiplexer to convert up to 32 channels of input from the amplification system to a 2 times 16 channels of data input for use by the data management and analysis system.

The foregoing objects and briefly described features of the electrophysiology system of the present invention are described with respect to the preferred forms of the present invention as set forth in detail below.

BRIEF DESCRIPTION OF THE DRAWINGS

Other features and advantages of the present invention will become more apparent with reference to the following description of the preferred embodiment and the accompanying drawings in which similar elements are represented by like numerals throughout, and in which:

FIG. 1 is a front view of a preferred embodiment of an integrated electrical signal switching and amplifying system formed in accordance with the principles of the present invention showing the front panel thereof;

FIG. 2 is a partial view of the back panel of the preferred embodiment of the integrated electrical signal switching and amplifying system;

FIGS. 4(a)–4(g), 5(a)–5(g) and 6(a)–(c) show the display of the preferred embodiment of the integrated electrical signal switching and amplifying system as configured in various modes of setup and operation;

FIG. 11 shows the display of the alternate preferred embodiment of FIG. 10 with the modified integrated electrical signal switching and amplifying system configured and constructed to include the real time display monitor installed therewith;

FIGS. 12(A)–12(H) show various displays of the modified amplification and real time display systems of FIG. 10;

DETAILED DESCRIPTION OF THE PREFERRED EMBODIMENTS

Figure 3:
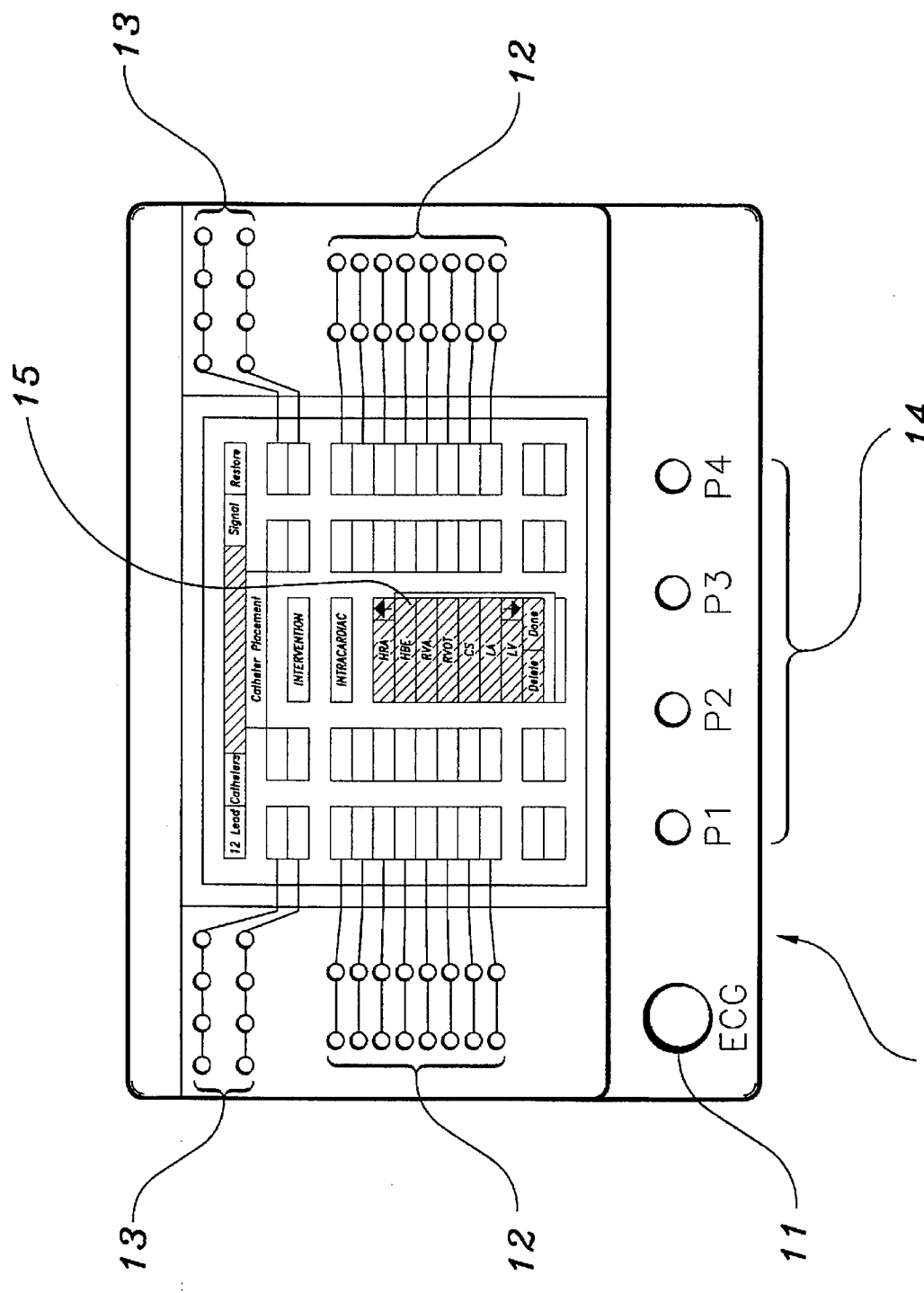
FIG. 3 shows the front panel of the preferred embodiment of the integrated electrical signal switching and amplifying system including the display thereof showing fields positioned thereon for containing labels corresponding to the referenced input terminals.

FIGS. 1–19 are provided as exemplary drawings to illustrate two preferred embodiments of a versatile electrophysiology system made in accordance with the principals of the present invention. As described more fully below and shown in the drawings, the system may include an integrated electrical signal switching and amplifying system (FIGS. 1–9) or a modified integrated electrical signal switching and amplifying system (FIGS. 10–19) referred to generally by the reference numeral 10, a real time display monitor referred to generally by the reference numeral 70, a data management and analysis system referred to generally by the reference numeral 180 an optional interface unit referred to generally by the reference numeral 182. Alternately, as also described below, the electrophysiology system may be configured to include a modified integrated electrical signal switching and amplifying system 10 and a real time display monitor 70 with a chart recorder or a modified integrated electrical signal switching and amplifying system 10 with a data management and analysis system 180 and a real time display monitor 70 and a chart recorder.

As shown in FIGS. 1–9, the preferred form of the integrated electrical signal switching and amplifying system facilitates the simplified setup and operation of an electrophysiology study.

More specifically, as shown in FIG. 1, the front panel of the amplification system 10 of the present embodiment includes a standard twelve lead ECG input terminal 11 which allows attachment of ECG lead cables through which leads extend from electrodes attached to the chest of a patient in a well known manner for transferring ECG signals into the amplification system 10.

Similarly, intracardiac input terminals 12 are positioned on the front panel, and include intervention/input terminals 13 which can be used as intracardiac input terminals or intervention (stimulation) terminals. The intervention/input terminals 13 are hard wired to corresponding intervention/output terminals 17 (as shown in FIG. 2). The intracardiac input terminals 12 are adapted to receive leads from the intracardiac catheters which have been placed within the patient's heart to sense the electrical signals passing therethrough. The intervention/input terminals 13 are designed to pass electrical stimulation signals (originating from an electrical stimulator, not shown) through the amplification system 10 into the intracardiac catheters. The intervention/input terminals 13 are also designed to receive electrical signals (originating in the heart) from the intracardiac catheters in the same manner as the input terminals 12.

Also included on the front panel are four pressure channel input terminals 14 which are designed for receipt of pressure sensor leads which have been attached to pressure sensors positioned at desired points on or within the patient's body from which blood pressure information is desired.

The dominant feature of the front panel of the amplification system 10 is an operator interactive "touch" display 15 which is programmed by an inboard microprocessor 27 (see FIG. 6) to operate as a labelling area for the input terminals 11, 12, 13, 14, and the auxiliary input terminals 16 (see FIG. 2). The display 15 is also configured by the microprocessor 27 to define touch areas thereon as "soft keys" for use in initiating setup and operation commands as will be explained below, and also to display messages related to setup and operation of the amplification system 10. Further, the display assignments of the output channels 17 (see FIG. 5A) and the labels, leads, gains, filter, and limiter settings through which each channel of entering data must pass when entered into the amplification system 10.

The display 15 is designed to simplify setup and operation of the amplification system 10 as will be explained momentarily. Software preprogrammed into the inboard microprocessor 27, such as by a ROM, is directly responsible for the operation of the display 15 and input "soft keys" thereof. The display 15 is preferably a single 640×480 pixel pressure responsive display commonly referred to as a "touch screen".

Although the present invention is not limited to the following, it is intended that the present embodiment of the present invention include the ability to receive ten leads of ECG signals as input into the input terminal 11 to allow a twelve lead analysis to be performed. Further, it is preferred that thirty-two intracardiac input terminals 12 and eight intervention or intracardiac input terminals 13 be included in the amplification system 10. Further, it is preferred that four pressure channel input terminals 14 be included with four auxiliary input channels 16 (See FIG. 2).

SETUP

Input Channel Selection

The display 15 is used to specify and setup labels associated with each input terminal 12, 13, 14, and 16. To describe the labeling process it is first necessary to define some terms. A label 28 (See FIG. 4(b)) is the alphanumeric assigned to an input terminal to identify the catheter or sensor and the lead attached thereto. A Catheter Group, or simply "group": is a group of labels 28 that have the same prefix letters but different numbers. An example of a Catheter Group would be: "RVA1, RVA2, RVA3, RVA4": (See FIG. 4(c)), where the prefix letters "RVA":, are common to each label 28 with the same base letters, regardless of their location on the display 15, belong to the same group. A field 29 (See FIG. 4(a)) is a label location on the display 15.

Figure 4A:
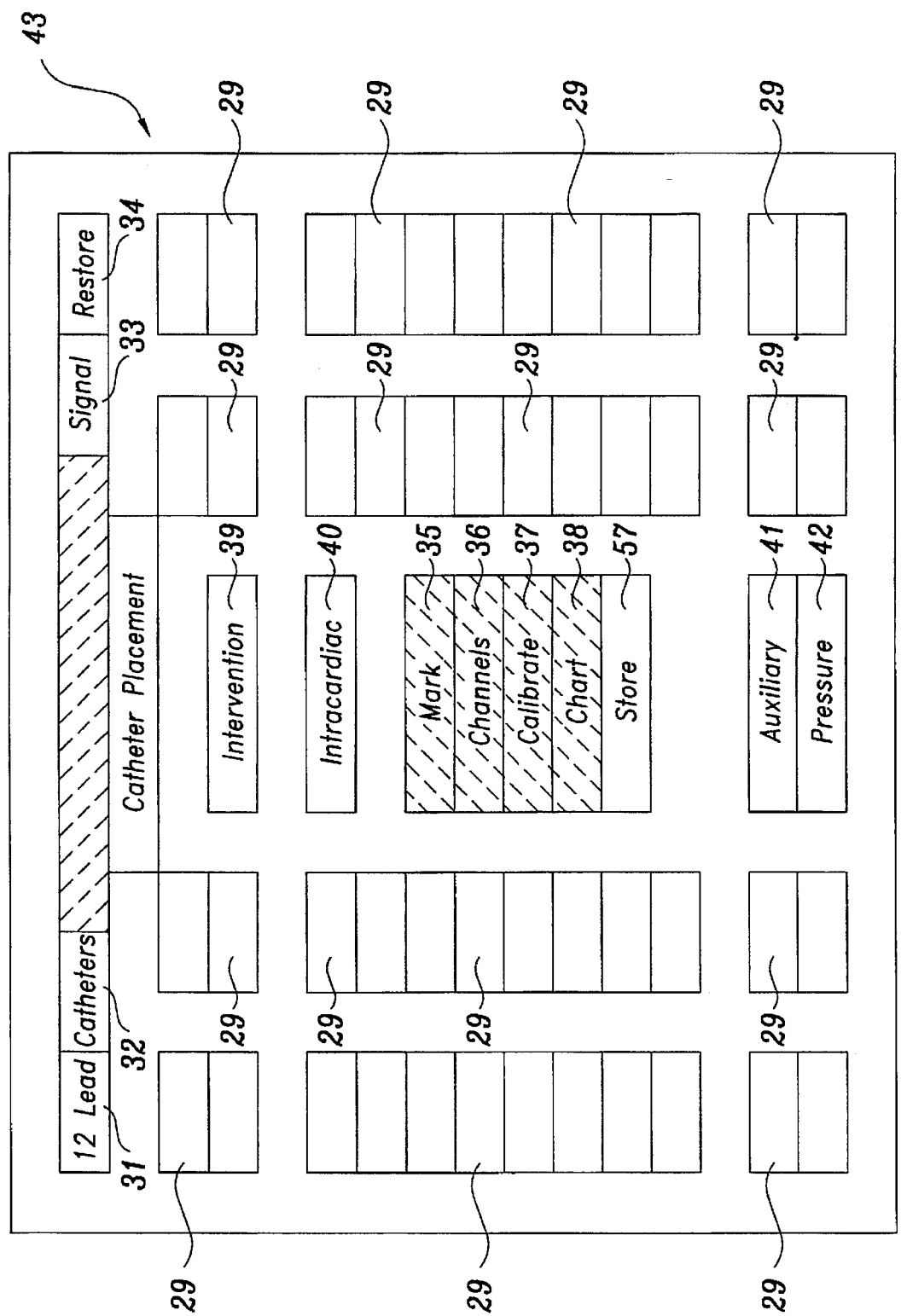
Figure 5A:
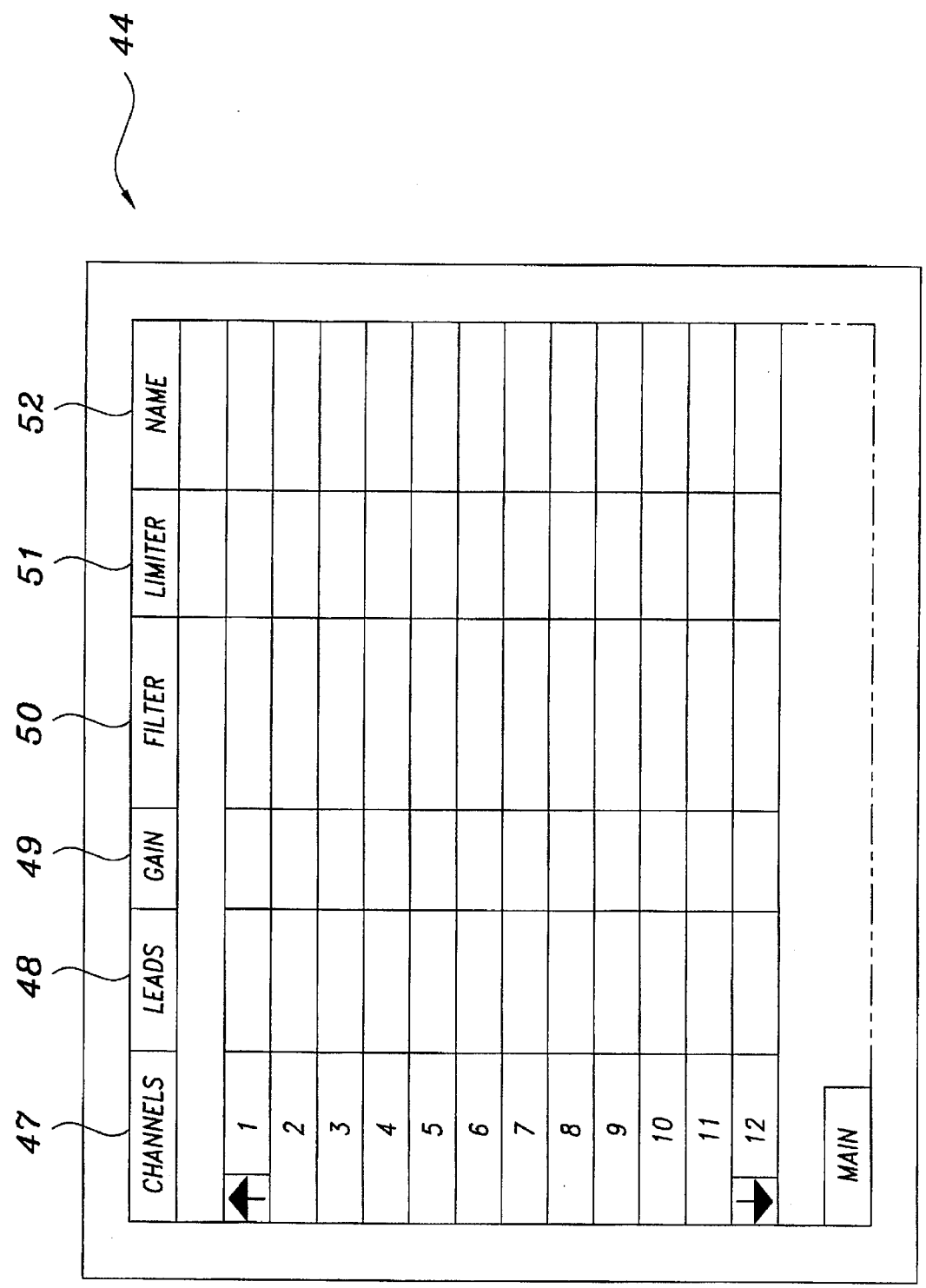
Figure 5B:
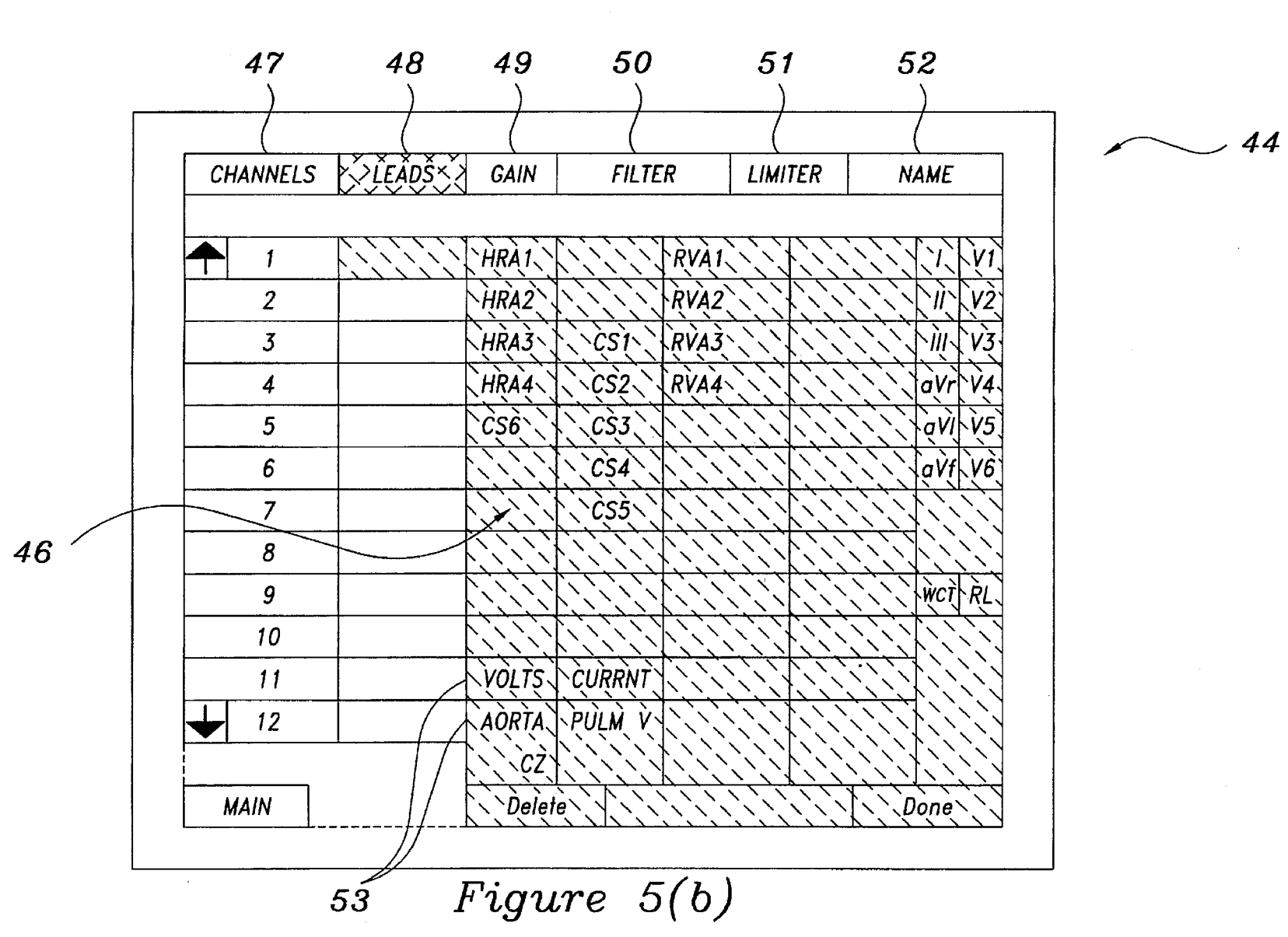
Figure 5C:
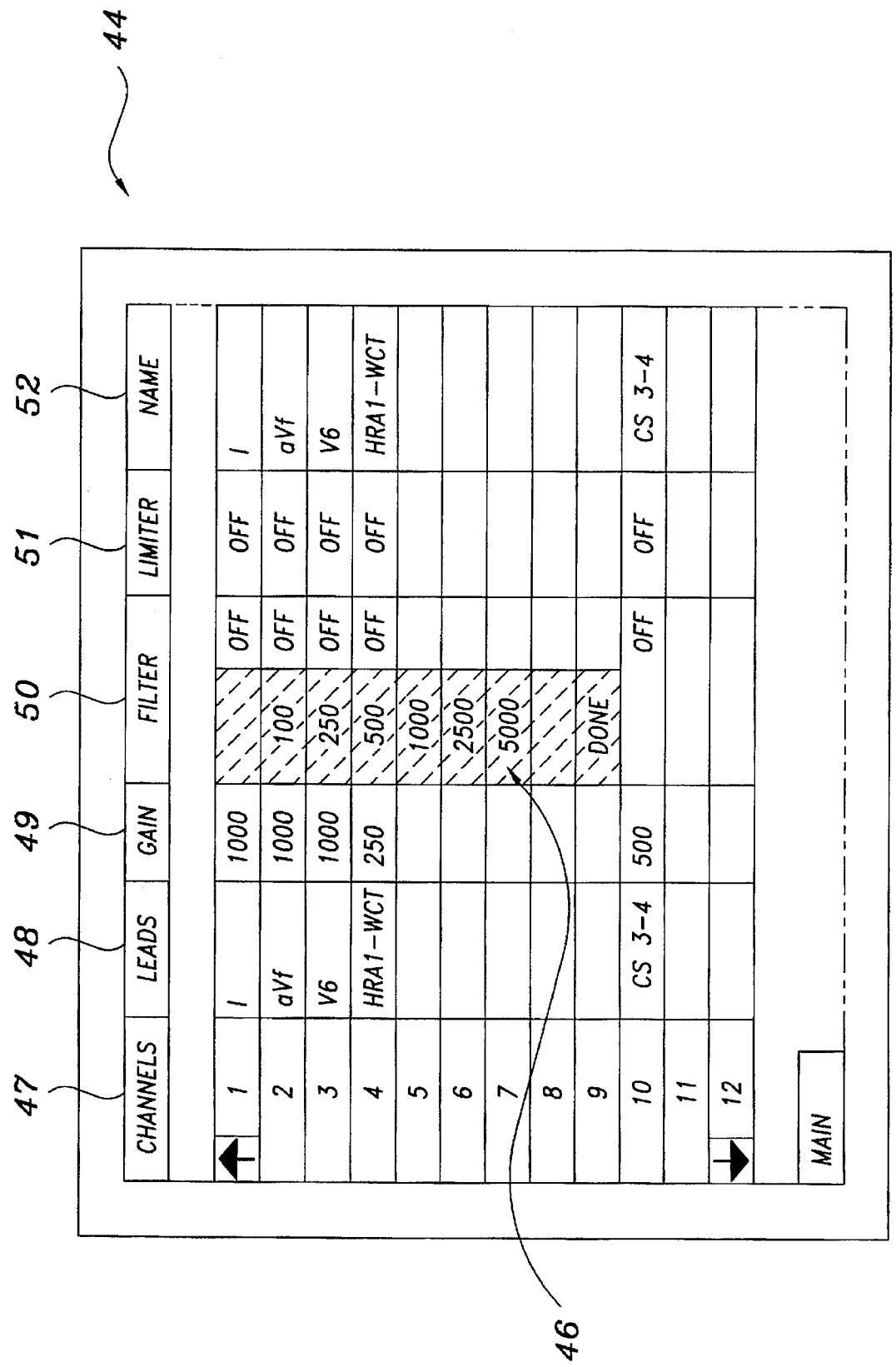

There are two basic screens which can be called to the display 15 by the operator to assist in arranging the setup configuration of the amplification system 10. The first is the "Catheter Placement Screen" 43 as shown in FIG. 4(a). The second is the "Signals Screen" as shown in FIG. 5(a). Once the electrophysiology catheters have been placed in the patient, setup of the amplification system 10 only requires the steps of: 1) Specifying the signal inputs by producing a label 28 for each one, and then 2) Specifying the desired signal output parameters. The first step is accomplished through the use of the Catheter Placement Screen 43, the second step is accomplished with the assistance of the Signals Screen 44.

Referring to FIG. 4(a), the Catheter Placement Screen 43 is preferably programmed from the following soft keys: a twelve lead key 31, a restore key 34, a catheter key 32, a signals key 33, a mark key 35, a channels key 36, a calibrate key 37, a chart key 38, an intervention key 39, an intracardiac key 40, an auxiliary key 41, and a pressure key 42.

Figure 4B:
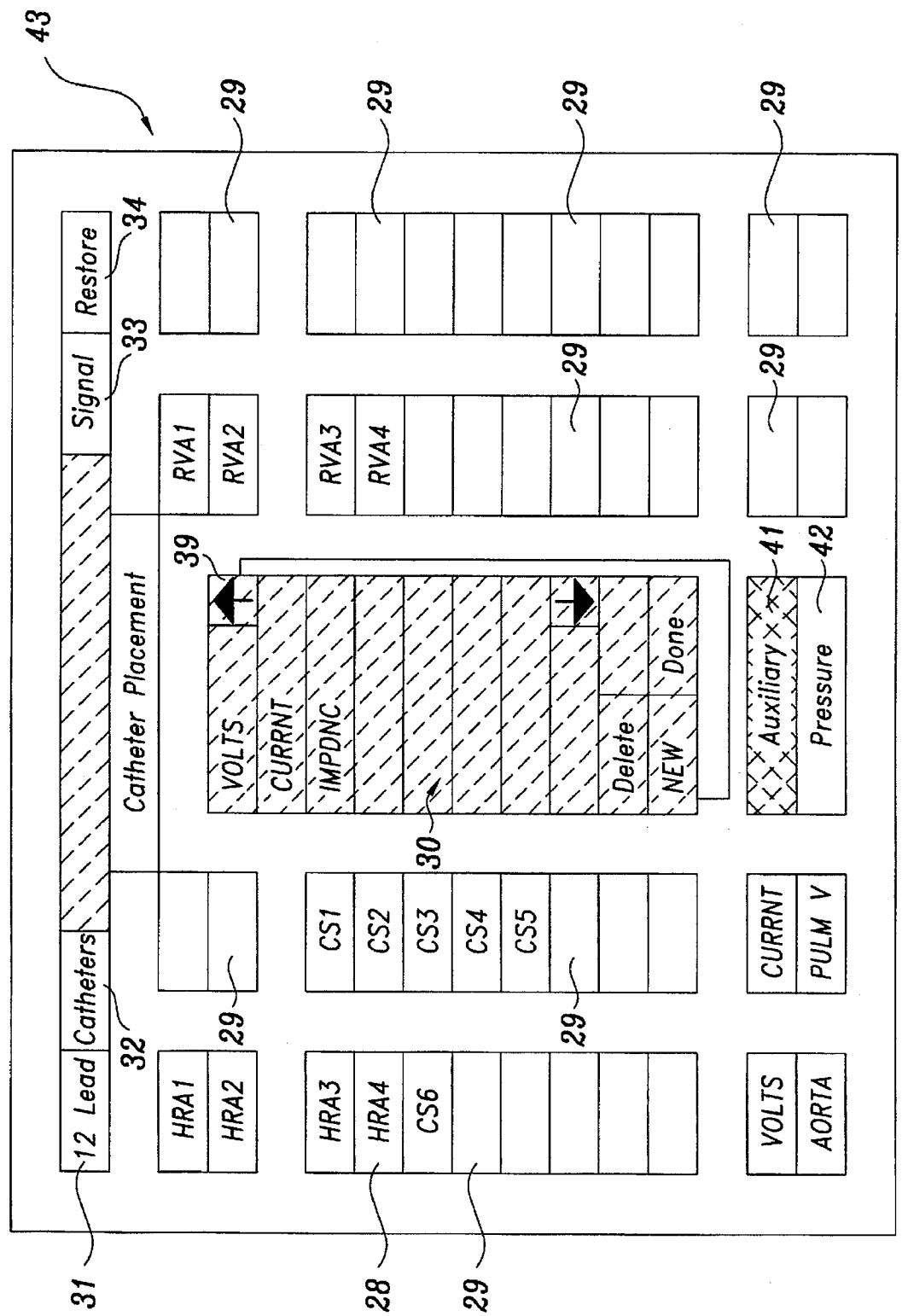

Briefly, to specify an input, the operator need only touch the key describing the input type, such as the intracardiac key 40, the auxiliary key 41, or the pressure key 42, then use the resulting directory 30 (See FIG. 4(b)) to assign each label 28 to the field 29 that corresponds to the correct lead input connector 12, 13, 14, or 16. To quickly assign a multiple of fields 29 to a single label 28, the operator touches the desired label 28 in the directory 30, then touches as many fields 29 as desired. Operating in this fashion to assign labels is hereafter referred to as the Batch Edit Mode of operation. To make a single assignment of a label 28 to a field 29, the operator first touches the desired field 29 and then touches the desired label 28 in the directory 30. Assigning a single label 28 at a time in this fashion is referred to hereafter as the Single Edit Mode of operation.

In Batch Edit Mode, when the user chooses which field or fields 29 to apply the label 28 to by touching in succession each desired field 29, the plural leads of the catheter or sensor will be automatically numbered appropriately. The operator can continue in this way for up to approximately 16 poles. If a field 29 was empty prior to this operation, the field 29 will be appropriately labeled. However, if there was already a label 28 present in the field 29, all associated labels 28 will be updated with the new label 28 and each lead connector will be numbered appropriately. When the operator is finished with one label 28, another label 28 may be chosen. When all desired labels 28 are assigned, the operator chooses "Done" from the touch screen, in which case the directory 30 will disappear. If the operator selects a field 29 which cannot possibly be assigned (such as choosing a pressure field while entering the title "Intracardiacs") an error message will be presented.

If the operator chooses an empty field 29 directly from the catheter placement screen 43, the directory 30 will appear, immediately placing the operator in the Single Select Mode of the setup operation. When the operator then makes a label selection, the locations directory 30 disappears and the new information is displayed in the previously empty field 29.

To move a catheter label 28 in the Single Edit mode, the operator chooses any one of the fields 29 containing the name of the catheter to be moved. All lead names of the catheter will then be highlighted, and the directory 30 will appear. The operator can then choose the new field 29 for the catheter, after which the directory 30 will disappear and the fields 29 will automatically be updated to show the new label 28.

Figure 4C:
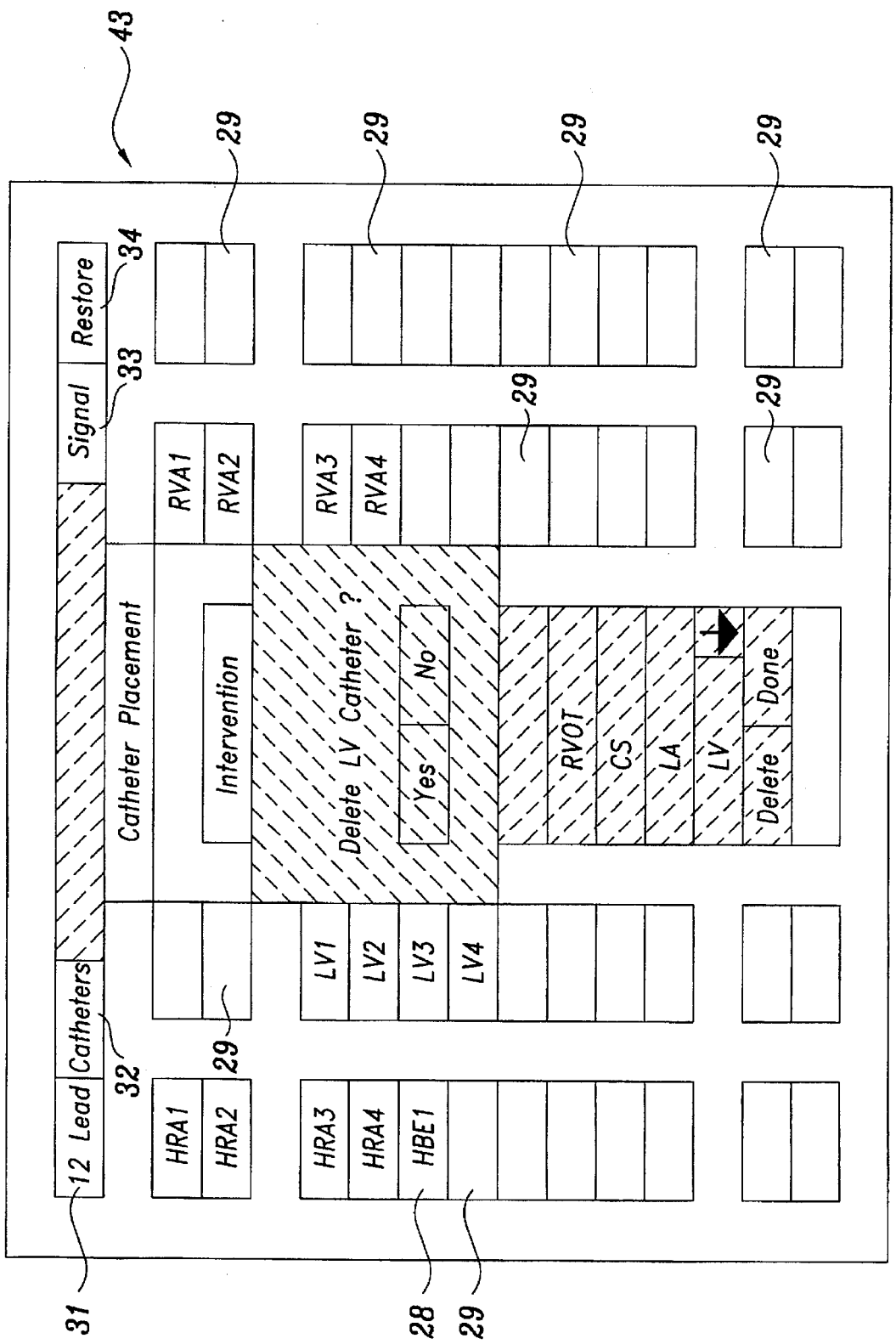

To remove a particular catheter in Batch Edit Mode, the user selects "Delete" from the directory 30 and then selects a field 29 associated with the particular catheter to be removed. As shown in FIG. 4(c), a screen containing the question "Delete XXX Catheter?" will appear. If the operator selects "Yes", all leads of the associated catheter will be removed. If the operator selects an invalid field 29, such as an empty field or fields 29 from Pressure or Auxiliary input terminals 14 or 16, an error message will appear. In Single Select Mode, the operator will have first chosen the field 29 to be highlighted, then will choose "Delete" from the directory 30. All leads of the catheter will then be removed as well as the confirmation question and the directory 30.

Figure 4D:
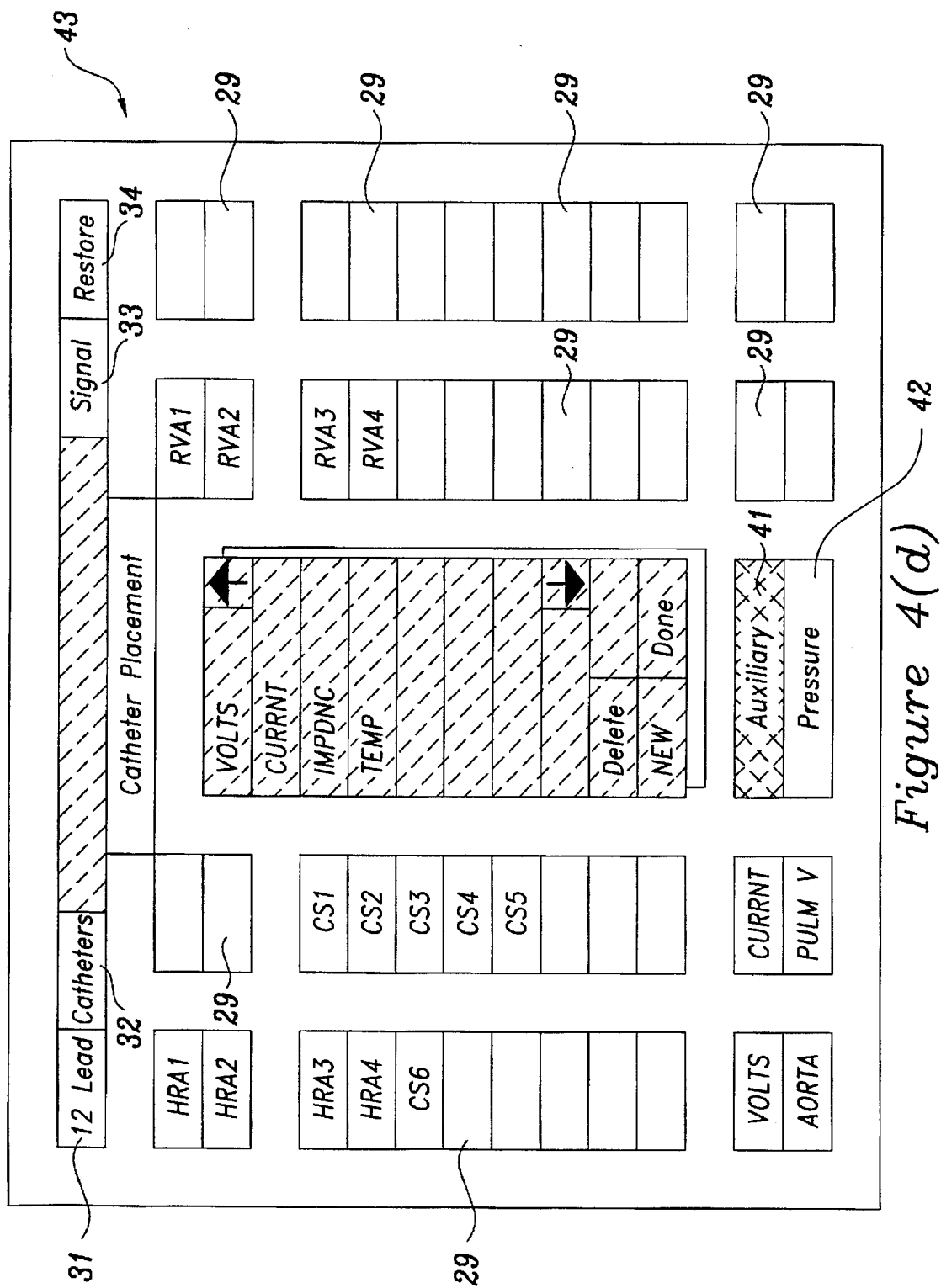

As shown in FIG. 4(d), the softkey "New" is available under the Auxiliary and Pressure directory 30 when in the Batch Edit Mode. When the "New" key is touched, it will be highlighted and the directory 30 containing a keyboard screen will be presented. The operator may then type in the desired new label 28 and touch "Done" to save the entry to the directory 30. The operator may then select this label 28 for use as input channel label.

While working with the Auxiliary or Pressure channels, the softkey "Delete" will also remove a label 28 from the directory 30. To do so, the operator selects "Delete", which will be highlighted, and then chooses the desired label 28 from the directory 30, A question confirming the operator's intent will appear and the label 28 will be removed if the operator answers "yes" to the confirming question.

Figure 4E:
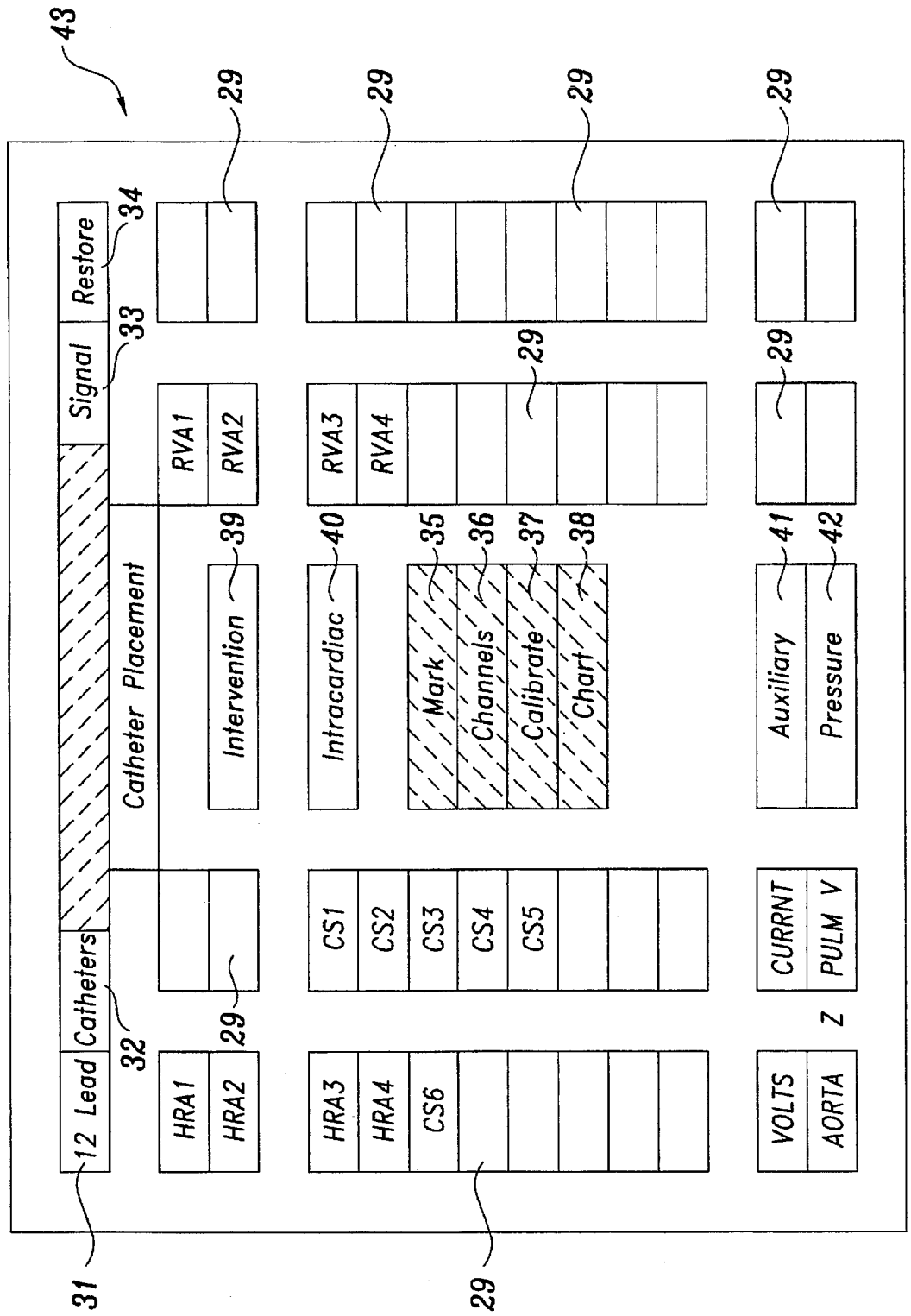

Zeroing of the Pressure channels 14 will also be available to the operator under the Pressure directory 30. The amplification system 10 will zero a Pressure channel 14 upon request from the user. If in the Single Edit Mode, the pressure sensor will be open to atmosphere prior to touching the "Zero" softkey. The amplification system 10 will then record the pressure signal for one second after the "Zero" key is touched and compute an offset value to be used to calibrate the channel. While zeroing is taking place the softkey will be highlighted. In the Batch Edit Mode, the operator chooses the "Zero" key and then chooses the desired input to be zeroed. The field 29 will then be highlighted while zeroing is taking place. After completion, in either Batch or Single Edit Mode, the letter "z" will appear to indicate that the channel has been zeroed as shown in FIG. 4(e).

Figure 4F:
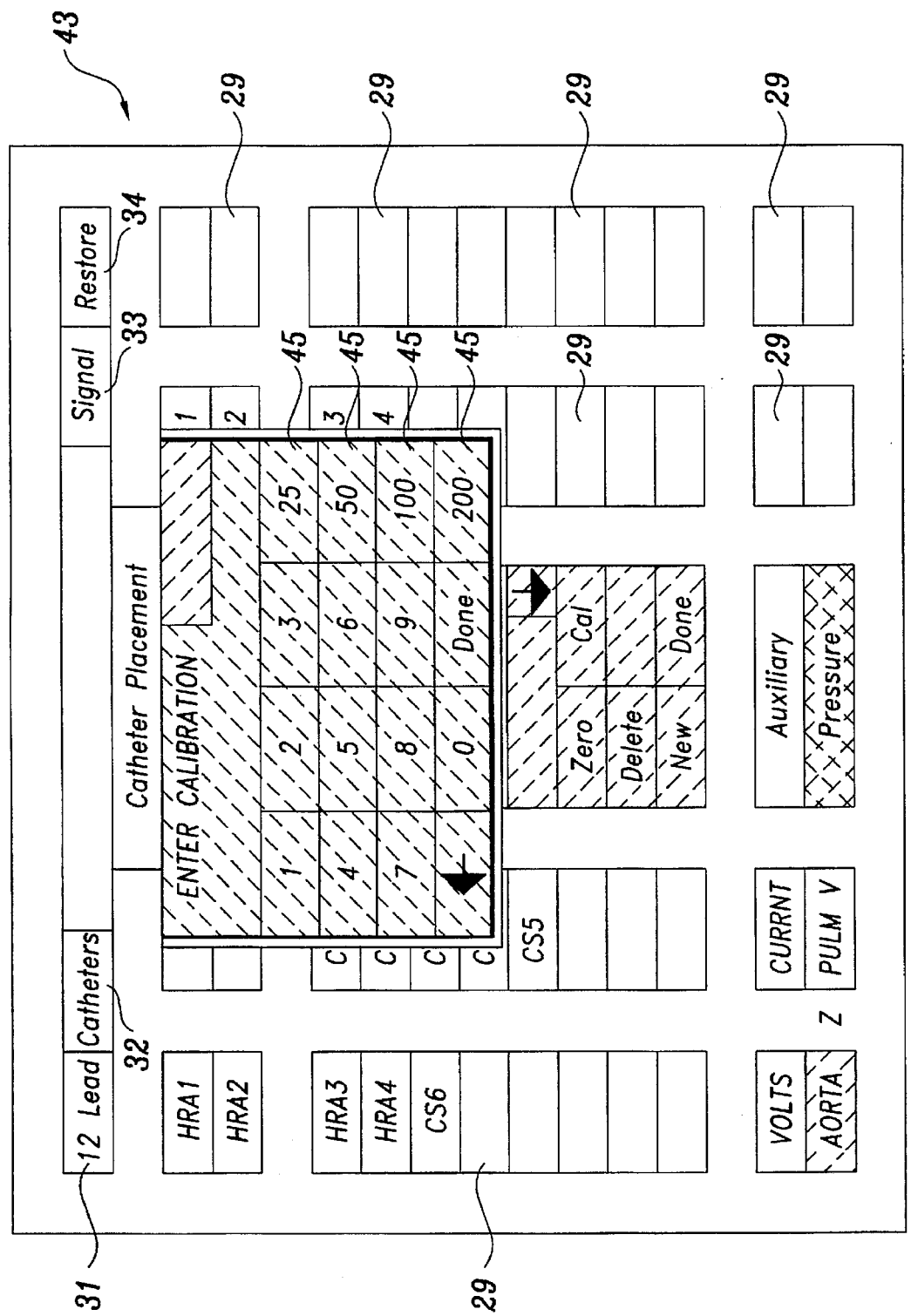
Figure 4G:
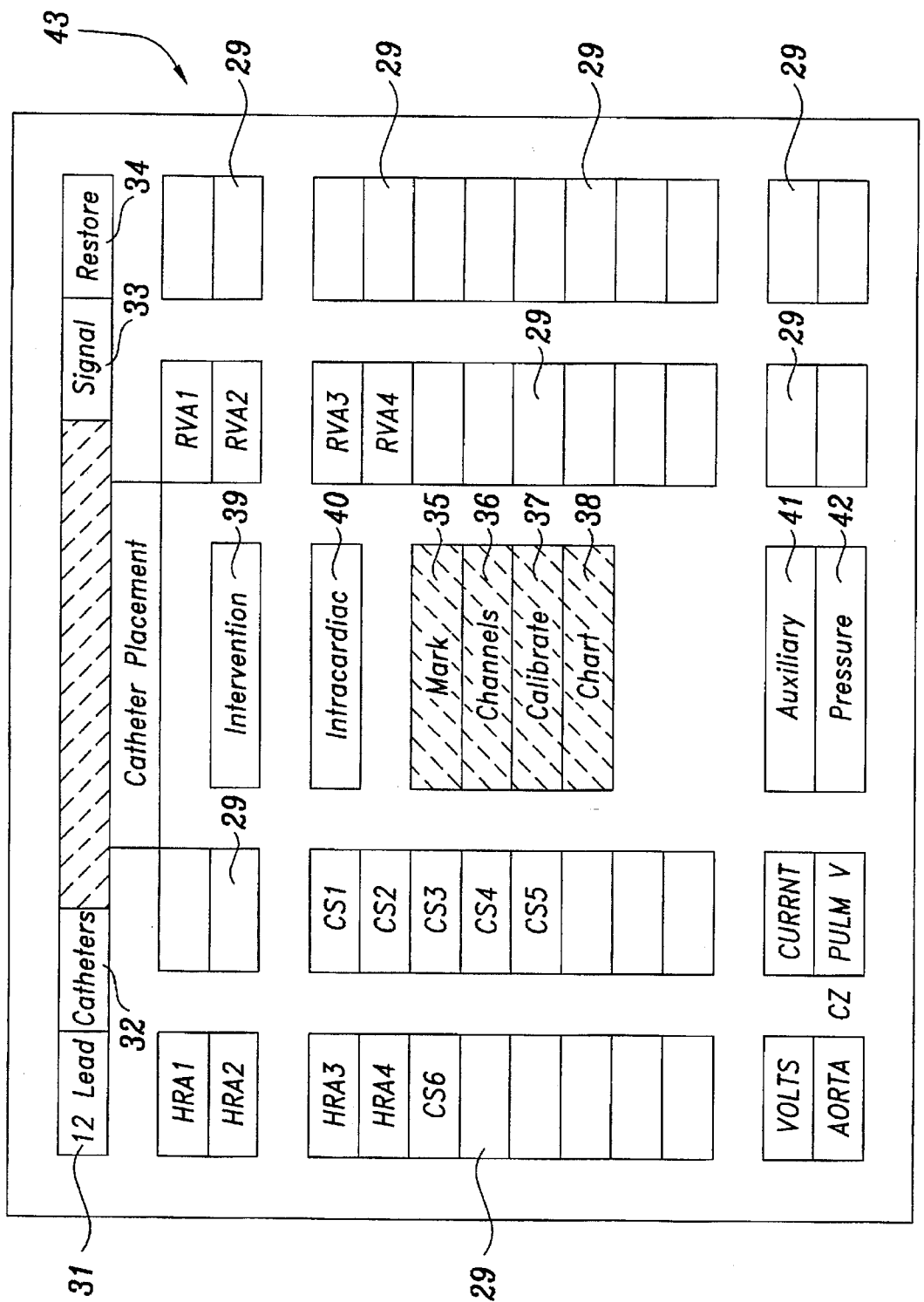

Calibration is available while setting up the pressure channels. The "Cal" key acts in a similar fashion as the "Zero" key as explained above. Once "Cal" has been touched, a numeric keypad directory 30 as shown in FIG. 4(f) will appear. The directory 30 will preferably contain four preprogrammed "Fast Cal" keys 45. The user then apples the calibrating pressure to the transducer and either enters the desired value or chooses one of the "Fast Cal" keys 45. Once calibrated, a "c" will appear in the box beside the label 28 corresponding to the calibrated channels as shown in FIG. 4(g).

Signal Selection

To select the desired output parameters to be associated with each channel label 28, the operator selects the "Signals" Softkey. At this point as shown in FIG. 5(a), the second of the two basic screens called the "Signals Screen" 44 will appear. The Signal Screen 44 contains a list of all assigned channels, their lead pairs, gains, filters, limiter level, and the output name of the channel which is to be used by the amplification system 10 for display purposes.

The Signals Screen 44 will behave in a manner similar to the Catheter Placement Screen 43 described above. The signals screen 44 is preferably preprogrammed with the following soft keys: channel key 47, leads key 48, gain key 49, filter key 50, limiter key 51, and name key 52. Also, the twelve lead key 31, catheters key 32, signals key 33 and restore key 34 are preprogrammed on the Signals Screen 44 in the identical manner as the Catheter Placement Screen 43.

When a soft key is chosen, the operator is immediately placed in the Batch Edit Mode of the setup operation. As shown in FIG. 5(b), a small "Items" screen 46, displaying information relative to the chosen soft key will appear. As used hereinafter, the term "items screen 46" will be used to generally identify the follow-up or popup screen which appears after an item has been selected. The operator chooses the desired item 53 or label 28 to be used from the item screen 46 and then chooses which field or fields 29 to apply it to. The operator can continue in this way indefinitely. When the operator is finished, "Done" can be chosen from the screen and the items screen 46 will disappear. Alternatively, if the operator chooses one of the fields 29 directly, the field 29 will be highlighted, and the items screen 46 will appear and place the setup operation into the Single Edit Mode. Once the operator selects the desired item 53, the items screen 46 disappears.

At any time the operator can choose the "Catheters" key 32 from the Signal Screen 44 and return to the Catheter Placement Screen 43, if desired. Similarly, at any time in the Catheter Placement Screen 43, the operator can choose the "Signals" key 33 and return to the Signals Screen 44.

Output Channel Selection

To begin filling out the desired combination of leads for output from the amplification system 10, the operator first touches the Leads key 48. The items screen 46 for Leads will appear as shown in FIG. 5(b) and contain a list of all available ECG, Intracardiac, Pressure and Auxiliary channels. Additionally, the ground leads "WCT" and "RL" will appear along with the softkeys "Delete" and "done".

In Single Edit Mode the user will have previously chosen the desired field 29 to edit and can now choose the label 28 to use to complete an output channel. By touching the desired label 28, the label 28 will appear in the highlighted field 29 previously selected (i.e. "RVA 1"). The operator's next touch will complete the lead pair and the label 28. If the completing pair is of similar type, then the label 28 will be automatically abbreviated to appear as a single prefix and a pair of lead numbers, such as "RVA 1–2". Otherwise the second half of the pair will just be appended and the label 28 will appear instantly. Once a pairing has been completed, the settings as previously indicated on the Signals Screen 44 associated with particular cardiac locations will be applied to the gain, filter, and limiter settings.

To edit the lead pair in Single Edit Mode, the operator touches the desired field 29 (which will be highlighted) and the items screen 46 immediately appears. The operator then touches the desired new labels 28 from the items screen 46. Of course, both labels 28 must be chosen again to compete the new lead pair.

To remove a label 28 in Batch Edit Mode, the operator chooses the softkey "Delete" from the Items screen 46. This will be highlighted and the operator then chooses the desired label 28. The label 28 will be removed from the screen as well as all other information for that channel. "Delete" will unhighlight after being used once. In Single Edit Mode the desired label 28 will already be highlighted and will be removed once "Delete" has been touched.

Gain and Filter Selection

In the embodiment shown in FIGS. 1–9, the gains and filters are pre-set to default values which can be changed by the operator if desired. To change the default gains or filters, the operator touches the desired default gain key 49 or filter key 50, and an items screen 46 appears as shown in FIG. 5(c) with all available gains or filter settings respectively. In Single Edit Mode, the operator will have previously chosen the field 29 to be edited and can now select the new item 53 from the presented list. The Item screen 46 will then disappear. In Batch Edit Mode the operator first selects the item 53 desired from the Item screen 46 and then selects all fields 29 it is desired to apply it to. The operator may continue in this manner until "Done" is finally selected. While adjusting filter settings, more than one item 53 may be chosen by the operator. These times 53 include High, Low and Notch filter settings. Each item 53 is highlighted as it is touched to indicate which items 53 have been chosen. If more than one item 53 in a particular section is touched, the highlight moves to the new item 53.

Limiter Setting

Figure 5D:
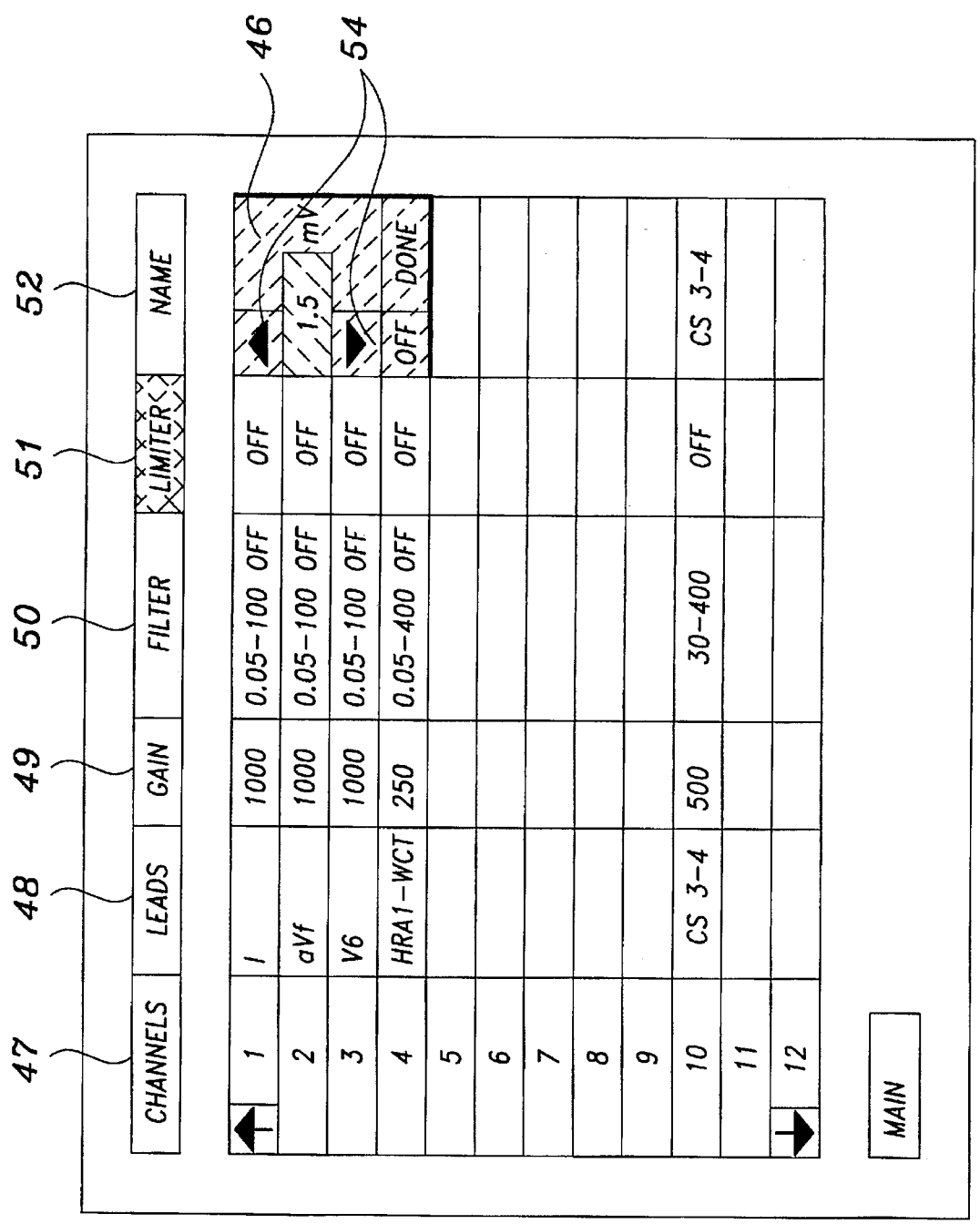

As shown in FIG. 5(d), the Limiter setting Items screen 46 presents a sliding scale to indicate the relative amount of limiting. To adjust the limiter setting, the operator touches the desired adjustment level 54 to choose the desired amount. The numbers placed in the appropriate filed 29 on the Signals Screen 44 corresponding to the limited reflect percentages of full scale. In Single Edit Mode there is a "Done" key on the screen 46 for the operator to indicate when the current level is correct. In Batch Edit Mode, the operator selects the amount of limiting and then applies it to the desired field or fields 29. "Done" is used to indicate when the operator has finished applying new limiting levels to all the desired channels. Limiting is applied in a bipolar fashion and is a +/– limit.

Channel Name Selection

Every channel preferably includes a name. The name fields are filled out with predetermined default names as the lead pairs are formed, the default name being the same as the label 28. However, the user can edit the name using the keyboard presented in the Name Selection screen 46, as shown in FIG. 5(e). Once completed, the operator can select "Done" and the keyboard screen 46 will disappear. In Batch Edit Mode, the operator types in the desired name and then chooses the desired field 29. Whatever is in the keyboard buffer 55 at the time the operator touches the desired field 29 will be used as the name. The operator then touches "done" to remove the screen 46 and exit Batch Edit Mode. Single Edit Mode is operated in a similar manner according to the general forma explained above for single edit mode operation.

Channel Number Editing and Channel Deletion

Channel editing may take place in either single or batch Edit Mode. As shown in FIG. 5(f) the operator selects the desired channel number to edit and the Items screen 46 appears with all the channels and their names, and the selected channel number is highlighted. Upon choosing a new channel which is not already in use the screen 46 will disappear and the channel will by moved to it's new position. The old position is initialized to an unused channel. If the operator selects a channel position from the screen 46 which is already occupied, the screen 46 will disappear, and the two channels will swap their configurations.

To remove a channel the operator selects "Delete" from the screen 46 and the previously selected channel will be removed.

An example of a completed Signals Screen 44 is shown in FIG. 5(g).

Catheter Placement Name Area

Figure 6A:
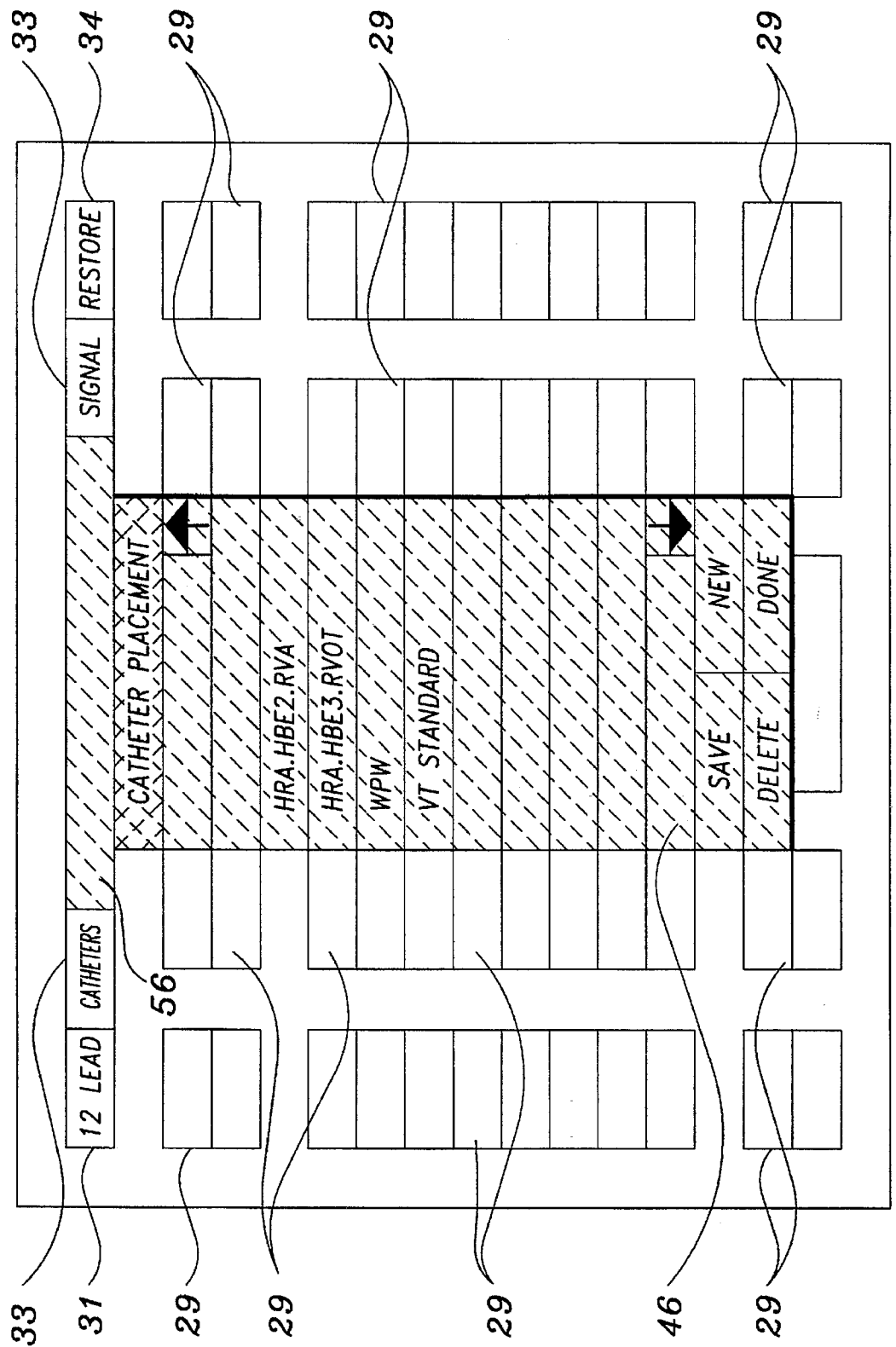
Figure 6B:
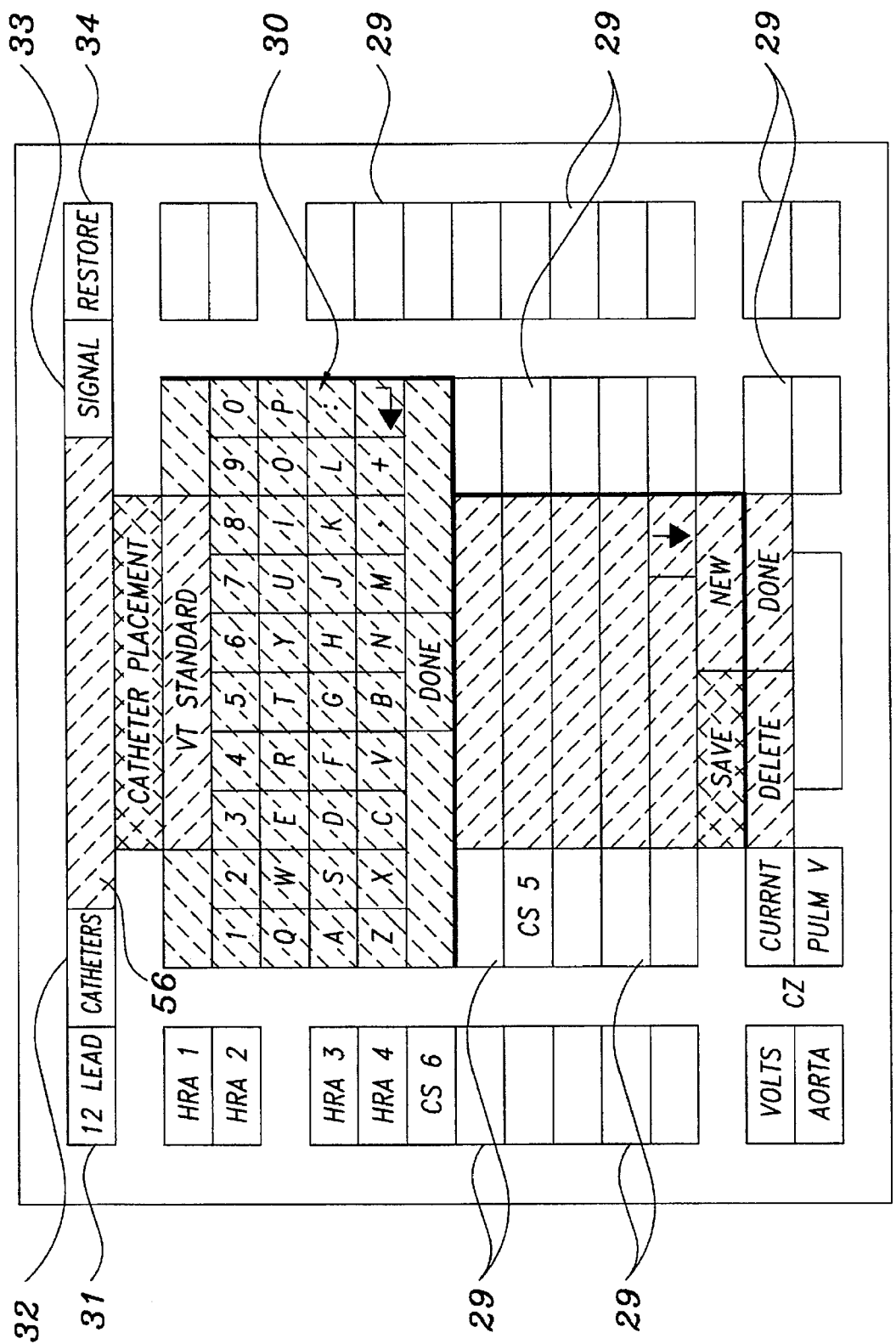

Referring again to the Catheter Placement Screen 43, as shown in FIG. 6(a), the "Catheter Placement Name" area 56 not only displays the currently invoked catheter placement name but is also active to the touch. Once the operator has completed preparations of the amplification system 10 for an electrophysiological procedure, the entire setup may be saved for recall later. To do this the operator simply touches the "Catheter Placement Name" area 56. If there is already a setup invoked, that setups name will be present in the area 56, otherwise the word "Setup" will appear. The operator is then present with the directory 30 containing a list of all available preset catheter setups as well as the softkeys "New", "Delete", "Save", and "Done". Upon selecting "Save" the operator is presented with the keyboard directory 30 as shown in FIG. 6(b) and is prompted to fill in the name of the current setup. If a previous catheter placement had been invoked, the operator is prompted to overwrite the old one or to create a new name. "Save" will be highlighted while active. The catheter placement setup will be saved both to the amplification system 10 memory and the computer processing unit if attached. To finish saving the operator selects "Done" from the keyboard directory 30.

Figure 6C:
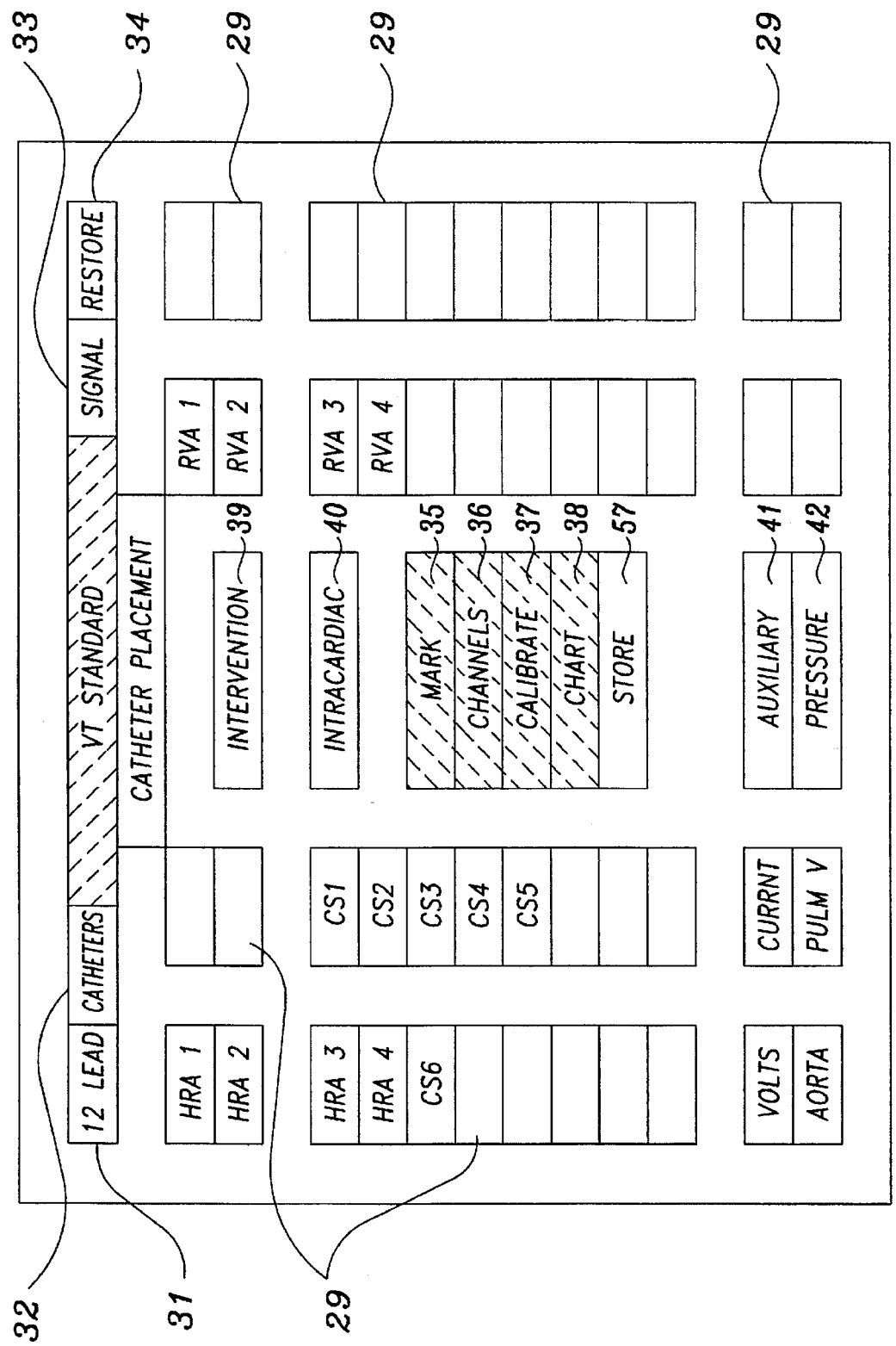

To invoke an old catheter placement the user touches the "Catheter Placement Name" area 56 and is present with the directory 30 containing the list of currently stored setups as again shown in FIG. 6(a). The operator then chooses the desired catheter setup by touching the desired name on the directory 30. The Catheter Placement Screen 43 will then be filled with that catheter setups' configuration such as shown in FIG. 6(c). If this is the correct catheter setup, the operator selects "Done" and the directory 30 disappears and the hardware is automatically reset with the new catheter setup configuration.

To remove a catheter setup configuration, the operator again initiates the catheter placement directory 30 and chooses "Delete". The operator then selects the setup to be removed, and the amplification system 10 asks for confirmation. Upon answering "Yes", the setup is removed. To return to normal operation the operator selects "Done".

To initialize the catheter Placement Screen 43, the user selects "New" which will clear all inputs and uninvoke the current catheter setup.

Twelve Lead Softkey and Restore Softkey

The "Twelve Lead" softkey 31, and the "Restore" softkey 34 are preferably located on opposite sides of the Catheter Placement Name area 56 on the Catheter Placement Screen 43 as shown in FIG. 6(a).

By touching the "Twelve Lead" softkey 31 the operator can toggle the first twelve outputs of the output terminals 17 to receive all ten ECG leads attached at the input ECG terminal 11. A popup 30 indicating that the twelve Lead ECG is being acquired will appear. The popup 30 contains a softkey containing the previous catheter placements name. To return to the previous placement the operator touches this softkey. If the placement has not yet been named, the softkey will contain "Return".

The "Restore" softkey 34 is used in the case that signals have drifted off of the computer real time display monitor or on the chart recorder, either from movement of the patient or from a defibrillation, and the operator wishes to remove the DC offset and place the signals back into the middle of the monitor. The Restore key 34 will by highlighted for appropriately one second to indicate that the signal placement is automatically being done.

Mark Softkey

The "Mark" key 35 is used to mark specific events in time during an electrophysiology procedure. "Mark" will by highlighted for appropriately one second after it is pressed to indicate to the operator that the mark is automatically being placed in the time record. Additionally, if the user is connected to the data management system but is not currently recording from the data management system and the user desires to mark an event, the data surrounding and including the desired event will be automatically recorded to the data management system.

Calibrate Softkey

The "Calibrate" key 37 is used to sent a square wave of 1 mV kHz (RTT) to all channels. Once pressed the key will be highlighted. To stop the calibration pulse the operator presses Calibrate key 37 again and the calibration stops. The highlight will also be removed.

Store Softkey

The "Store" key 57 is used to initiate storage of data. Recording will start from five seconds previous to when the store key 57 is touched, and storage thereafter is continuous. The operator will be able to stop storage by touching the store key 57 again.

Chart Softkey

The "Chart" key 38 delivers start and stop signals to the chart recorder if attached to the system. While active, the "Chart" key 38 will remain highlighted. To stop the chart recorder, the operator simply presses Chart key 38 again.

Automatic DSP Calibration

Figure 7:
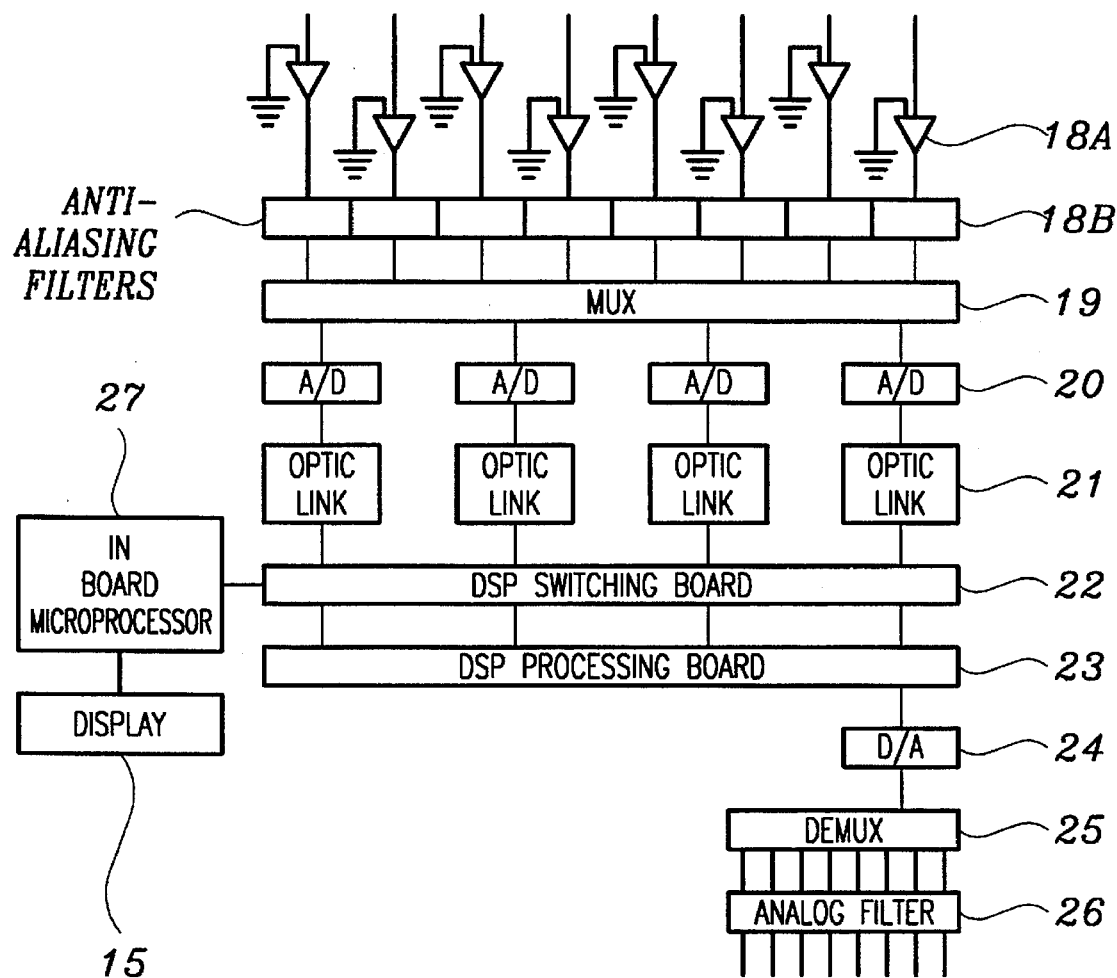
FIG. 7 is a block diagram of the internal electronics of the preferred embodiment of the integrated electrical signal switching and amplifying systems.

Referring now to FIG. 7, if the gain or phase response of the front-end amplifiers 18A are not identical, then the digital signal processor (DSP) 22 will not eliminate all of the common mode signal during the common mode signal rejection operation. Therefore, an automatic calibration system is included in the amplification system 10 of the present invention to automatically digitally calibrate the front-end amplifiers 18A prior to the initial use of the amplification system 10 in order to correct for any nonuniform phase or gain performance between the front-end amplifiers 18A.

The automatic calibration is performed by attaching a cable (not shown) from the output channels 17 to all of the Intracardiac input channels 12 in parallel. The operator then enters the "Calibration Mode" of the amplification system 10 and the DSP 22 automatically enters a known signal at each input channel 12 through the attached cable.

The DSP 22 then samples the gain and phase of the signal it receives from each of the front-end amplifiers 18A. The difference between the gain and phase value of the known signal and the gain and phase value of the signal as received by the DSP 22 after passing through each front-end amplifier 18A is then digitally stored by the amplification system 10 in a table. Thereafter, during normal (non-calibration mode) operation of the amplification system 10, each signal received by the DSP 22 from the front-end amplifiers 18A is corrected by the stored digital value corresponding to the difference between the known calibration mode signal and the received signal of each front-end amplifier 18A. In this manner, any common mode signal received into the DSP 22 will be completely rejected regardless of which inputs 12 are used.

Since the automatic calibration values are stored digitally in a table in the amplification system 10, they do not experience any significant drift over the normal life of the amplification system 10. Calibration of the front-end amplifiers 18A therefore is intended to be necessary only as an initial calibration, i.e. one time calibration before initial use of the amplification system 10. Since this automatic calibration need be performed only once, it can be performed by the manufacturer of the amplification system 10 and the subsequent operator will have no need to be concerned with it during normal use.

OPERATION

The block diagram of FIG. 7 generally shows the preferred architecture of the internal electronics of the present invention. Up to sixty-four electrical inputs from the input terminals of the amplification system 10 are passed through front-end amplifiers 18A and anti-alias filters 18B and then directly into a multiplexer 19. The signals are multiplexed into four output channels carrying sixteen input channels each and passed through A/D converters 20 and optical links 21 into the DSP switching board 22. The DSP 22 operates as a switching matrix, such as in the manner of prior art analog switching matrixes, except that instead of switching analog signals electronically into differential amplifiers, the DSP 22 of the present invention switches digital signals and operates itself as an "differential amplifier". This is done by electronically combining the digital representations of each signal, such as by subtraction, which results in sixteen output channels (or thirty-two output channels if desired) which pass directly into a DSP processing board 23 (or two DSP processing boards in the case of thirty-two channel outputs form the DSP switching board 22).

As is readily evident, the DSP switching board 22 of the present invention has been configured for operation to eliminate common mode signals from raw, digitized analog input signals. In this manner, the present invention is distinguished from any prior art use of digital signal processors since common mode signal noise is removed by prior art systems before any digital signal processors are utilized. The prior art use of digital signal processors has been simply to process signals which have previously been passed through an analog switching matrix. In these prior art systems, the common mode rejection function on the analog signals has already been performed through known techniques using differential amplifiers. In the present invention however, the DSP switching board 22 itself operates as a differential amplifier to perform the signal switching operation and to do common mode rejection on the raw digital signals.

The signals received by the DSP processing board 23 are processed for gain, signal limiting and the application of a plurality of filters thereto. Each DSP processing board 23 (one in the case of sixteen output channels from the DSP switching board 22, and two in the case of thirty-two output channels from the DSP switching board 22) outputs a single multiplexed channel to a D/A converter 24 which is then passed through a de-multiplexer 25 to restore sixteen channels. These are then passed through an analog filter 26 to the output 17 of the amplification system 10.

The DSP switching board 22 and DSP processing board or boards 23 are driven by an onboard microprocessor 27 which is also operationally attached to the display 15.

In constructing the amplification system 10 of the present invention with the DSP switching board 22, a large amount of bulk is eliminated, thus allowing the amplification system 10 to be significantly reduced in size compared to prior art hardware.

Also, the utilization of the DSP processing board 23 for filter, limiter, and gain application significantly aids in downsizing the overall physical dimensions of the amplification system 10 by allowing elimination of the prior art type filter blocks which for each signal channel. The result is a amplification system 10 which is significantly smaller that prior art hardware and which is therefore conveniently positionable directly at the patient's bedside to allow bedside control of the amplification system 10 by the operator during setup and electrophysiology procedures.

The amplification system 10 of the present invention can be attached through its output ports 17 by a cable to a real time display monitor 60, a computer processing unit such as the data management and analysis system 110 described below, and/or a chart recorder and an interface unit 160. An example of a computer processing unit usable with the amplification system 10 of the present invention is manufactured by Quinton Electrophysiology Corporation of Markham, Ontario, Canada, and is presently being marketed under the trademark "EPLab".

Since the DSP switching board 22 is used for common mode rejection, it is very advantageous in the present invention to employ A/D converters having very high resolution, such as sixteen bit resolution.

The preferred gain ranges for the embodiment of the amplification system 10 shown in FIGS. 1–9 include gain ranges of 100 to 5000 for ECG, intracardiac and pressure channels, and gain ranges between 1 and 5000 for the auxiliary channels. The amplification system 10 employs three different filters, including high pass filters in the range of DC, 0.05 Hz, 1.0 Hz, 10 Hz, and 30 Hz, low pass filters in the range of 40 Hz, 100 Hz, 200 Hz, and 400 Hz, and notch filters in the range of 50 or 60 Hz. The common mode rejection level is preferably greater than 100 DB.

Figure 8:
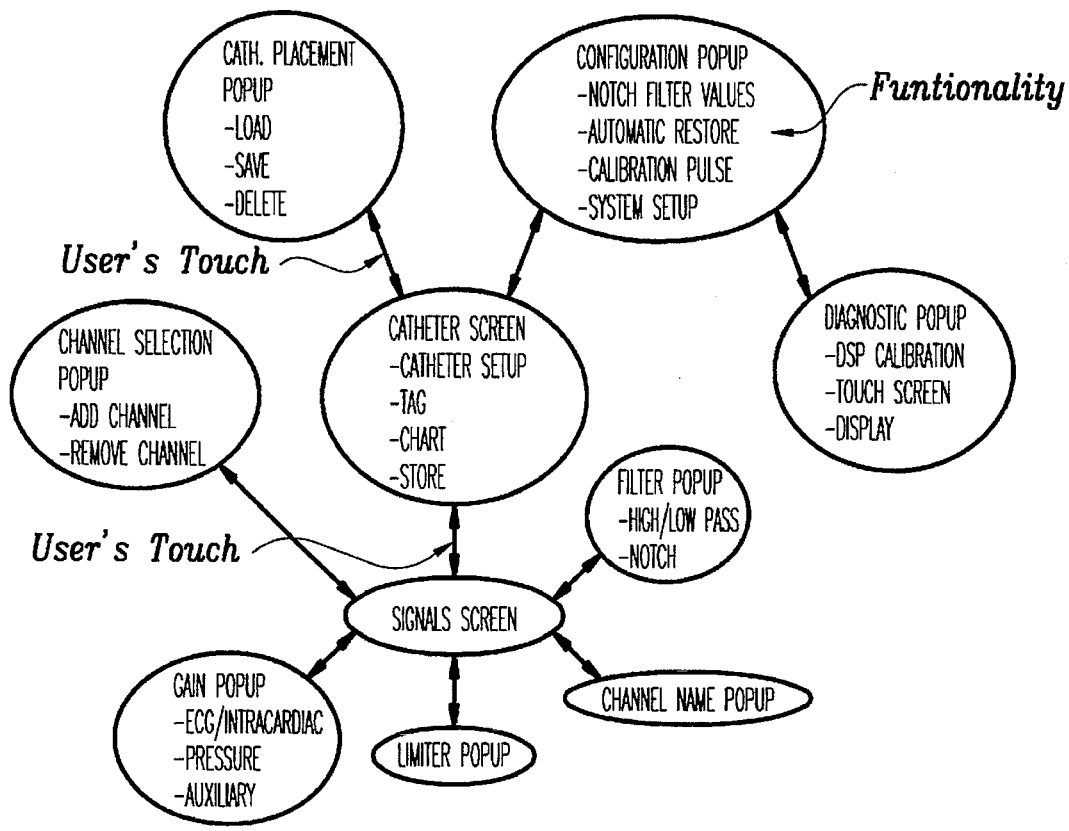
FIG. 8 is a block diagram of the screen organization of the integrated electrical signal switching and amplifying system in the configuration and construction shown in FIGS. 1–7.
Figure 9:
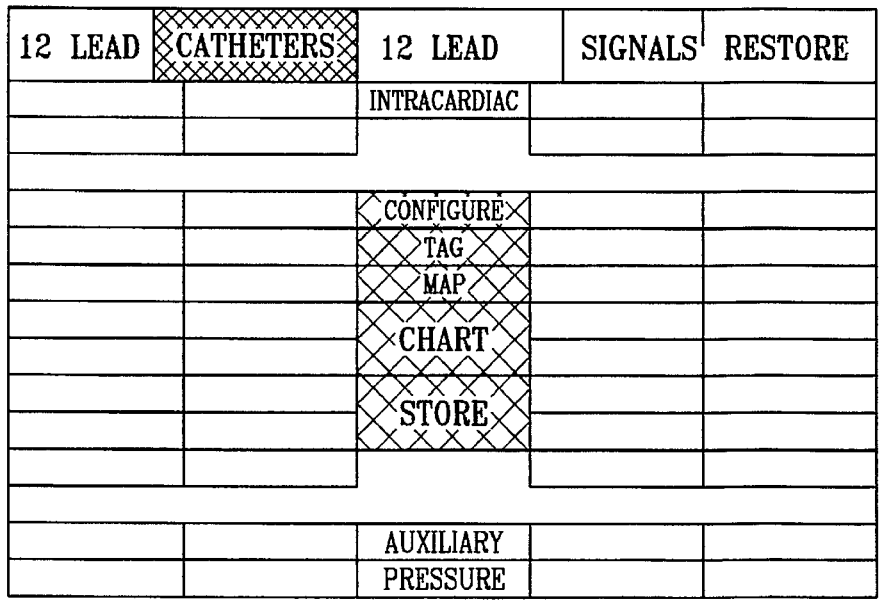
FIG. 9 shows the display of an alternate preferred form of the Catheters Screen of the integrated electrical signal switching and amplifying system as configured and constructed in accordance with the embodiment of FIGS. 1–7.

FIG. 8 illustrates an alternate form of the screen organization for the modified amplification system 10 of the present invention where the real time display monitor 70 is not installed. In this embodiment, the user will have access to two primary screens and the operation thereof is generally similar to the operation of the screens described above. As shown in FIG. 8, access to the Filter, Gain, Channel Selection, Name Screen and Limiter Screens is directly from the Signals Screen 50. Additionally, access to the Catheter Placement and Configuration (Diagnostic) Screens are available directly from the Catheters Screen 52 as shown in FIG. 9.

As described above, the Catheter Screen 52 is used to setup the catheters and functions as the main screen during a procedure. As shown in FIG. 9, when the real time display monitor 70 is not installed with the modified amplification system 10, the Catheters Screen includes the 12 Lead default setup, Catheters Setup, a go to Signals Screen 50, Restore (to return all signals to baseline), ECG/Intracardiac Catheter Setup, Configure analysis system, Mark data (to mark log entries), Chart, Store, Auxiliary, Pressure and Map screen options.

FIGS. 10–19 are illustrative of an alternate preferred form of the present invention. As described herein, the improved electrophysiology system of FIGS. 10–19 includes a modified amplification system 10 which provides the user with the ability to control the real time display monitor 70 and chart recorder from the bedside or through the data management and analysis system. The modified amplification system 10 referred to herein retains many of the basic features described above with respect to FIGS. 1–9 and includes the additional features and improvements described below. The electrophysiology system described herein provides a redundant control mechanism when the modified amplification system 10 is used with the data management and analysis system 180 or another compatible central processing unit, such that if either of the systems malfunction during the procedure, the physician may continue the study because of the ability to control the real time display monitor from either or both systems. Additionally, the modified amplification system 10 allows the user to select the filter settings desired for the particular patient or study rather than relying on preset filter settings.

The real time display monitor 70 of the present embodiment also provides for a 32 channel electrophysiology system which is controllable at the bedside of the patient to provide 32 channels of data which may be viewed in either the panning or scrolling mode as selected by the user. Similarly, the real time display monitor display provides a triggered sweep mode which may be used to overlay the data displayed on the digital real time display monitor.

Figure 10:
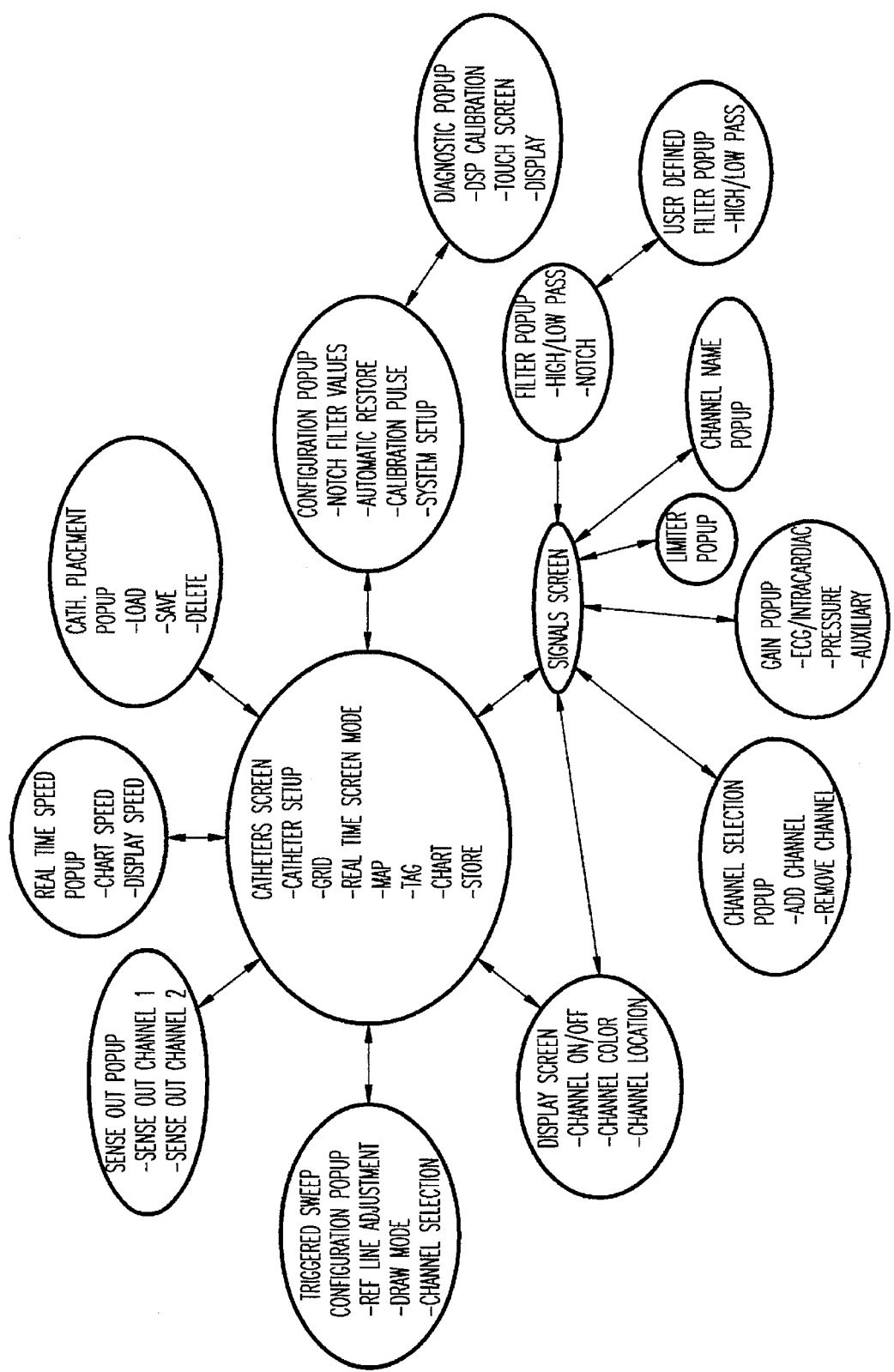
FIG. 10 is a block diagram of the screen organization of an alternate and preferred form of the electrophysiology system of the present invention having a modified integrated electrical signal switching and amplifying system with a real time display monitor operational therewith.

The screen organization format shown in FIG. 10 provides an alternate preferred form of screen organization for the modified amplification system 10. The screen organization format for use with the modified amplification system 10 with the real time display monitor 70 is different from the screen organization as shown in FIG. 8. With the real time display monitor 70 operatively connected to the modified amplification system 10, the user is able to access the Catheter Placement, Configuration (diagnostics), Triggered Sweep Reference Line Adjustment, Triggered Sweep Channel Selection, Sense Out and Real Time Speed Screens directly from the Catheters Screen 52. Additionally, the user will be able to directly access the Display Screen 54 from either of the Signals Screen 50 or the Catheters Screen 52.

As shown in FIG. 11, the Catheters Screen 52 for the modified Amplifier System 10 with the real time display monitor 70 includes additional options for the user as compared to the Catheters Screen 52 shown in FIG. 9. These additional options relate to the functions of the real time display monitor 70 and include the options to control the speed for the chart and real time display monitor, an on/off grid display, a scroll display mode, a sweep display mode, a triggered sweep display mode, a channel selection for the triggered sweep, a reference line adjustment for the triggered sweep, a pair of sense out signals to synchronize external devices, full screen, horizontal split screen and vertical split screen options, a chart recorder toggle and a map to copy the contents of the dynamic screen to a static area and create a map entry in the data management and analysis system.

Figures 12D, 12E:
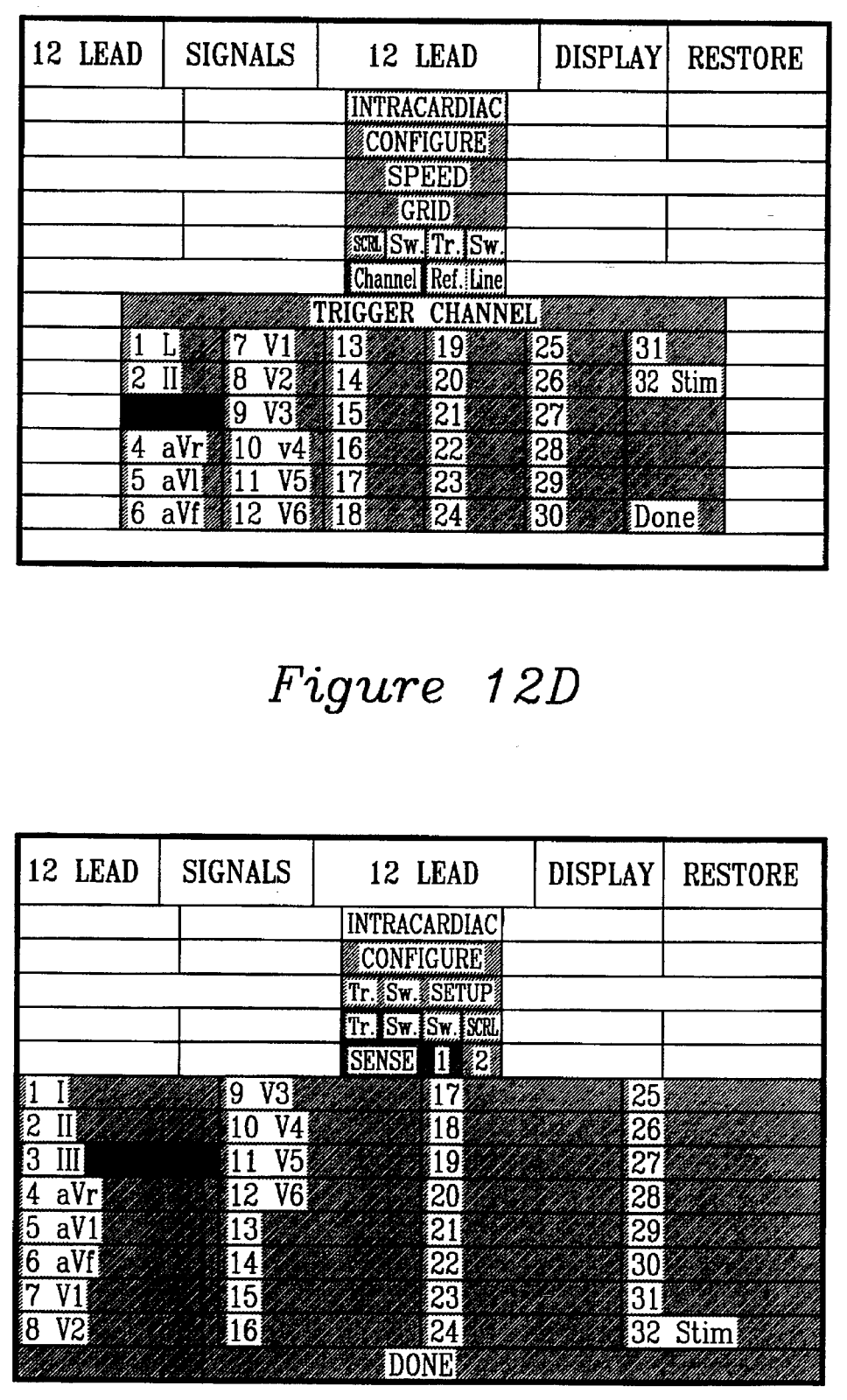

As shown in FIG. 12 A, the speed control option 56 is highlighted when it is active and is used to change the speed of the real time display and the chart recorder. This option continually receives input relating to the status of the speed button, the current chart recorder speed and the current display speed. Although the speed of the real time display and chart recorder may be programmed to operate at any desired settings, the speed option displays the user selectable values of 25, 50, 75, 100, 200, and 400 for the real time display speed and highlights the current speed. The speed option also displays the user selectable values of 25, 50, 75, 100 and 200 for the chart recorder speed with the current speed being highlighted. The chart recorder continuously prints the real time wave form signals from the amplification system 10 for the selected channels of the surface ECG, intracardiac, auxiliary or pressure catheters as long as the operation thereof is enabled. Additionally, the chart recorder prints the channel labels, the grid and the paper speed on every page.

As shown in FIG. 12 B, the configure option 58 is highlighted when it is active and provides the user with further options to select the notch filter frequency, auto restore, calibration, diagnostics and system setup. The configure option receives input relating to the notch filter frequency and the on or off status of the auto restore option. The notch filter frequency for the modified amplification system 10 is selectable by the user through this option for 50 and 60 Hz operation. The auto restore option automatically restores the signals to baseline following defibrillation using a predetermined filter and other parameters. The calibration option sends out a 1 mV or 0.1 mV user selectable square wave calibration pulse. The diagnostics option performs self diagnostics for the modified amplification system and the systems setup option identifies current version numbers of the hardware, firmware and software of the amplification system.

As shown in FIG. 12 C, the triggered sweep reference line adjustment option 60 includes a vertical reference line on the real time monitor to provide the user with a wave comparison when the display is in the triggered sweep mode and also provides the user with the option of using either an erase or overlay type of triggered sweep. It is believed that none of the prior digital real time display monitors included the capability of providing the user with the ability to select the overlay type of triggered sweep as described herein.

As discussed above, the amplification system 10 controls the operation of the real time display monitor 70. The display of the wave form data is controlled by the amplification system 10. The modified amplification system 10 allows the user to select the display of the wave forms in one of four modes as well as in a freeze frame mode. The most commonly used mode is the scrolling or panning mode where the real time wave form data is displayed on the monitor from the right to the left at the selected scrolling speed. In the preferred form of the present invention, the scrolling speed is selectable between a minimum speed of 25 mm/sec and a maximum speed of 400 mm/sec in 25 mm/sec increments. Another mode which may be selected by the user is the sweep mode. In this mode the real time wave form data is constantly displayed across the monitor using a sweeping vertical bar that travels from the left to the right at selected panning speed. In the preferred form of the present invention, the minimum width of the vertical bar is 4 pixels and the maximum width of the vertical bar is 16 pixels. The sweep bar travels across the monitor between a minimum speed of 25 mm/sec and a maximum speed of 400 mm/sec which is selectable by the user in increments of 25 mm/sec.

In the triggered sweep mode, the vertical bar only sweeps when it detects a valid triggering signal from the selected channel. The trigger channel is selectable between channels 1 and 32 and the type of trigger events are also selectable and include the detection of R wave transitions or stimulation pulses. In this mode the amount of delay from the triggering event is also selectable and the sweep may performed as an erasing or overlay type of display wherein the prior data is either erased as the vertical bar passes across the screen or is displayed over or overlays the prior data.

The final mode is the split screen mode and the user may select the split screen as either the horizontal or vertical mode. In this mode, one of the split screens will be frozen while the other portion of the screen will continue as a scrolling or sweeping display.

As shown in FIG. 12 D, the trigger channel selection option 62 is used to select the channel that will trigger a sweep on the real time display monitor and also highlight the currently selected channel.

As shown in FIG. 12 E, the sense out channel option 64 relates to normal output channels that are used to synchronize external devices such as stimulators to the wave data.

FIG. 12 F shows the option to display the results on the real time display monitor 70 in a representation of Millivolts per centimeter and on the chart recorder that takes the input from the modified amplification system 10 to the real time display monitor 70 and scales it to centimeters on the paper of the chart recorder. In this embodiment, the chart recorder prints the real time data whenever the user has selected the chart recorder. With the Millivolts per centimeter option 66, the user may depress the gain button to display a screen with the gain factors for the ECG/Intracardiac calibration factors in the range of 0.05 mV/cm to 20 mV/cm including values of 0.05 mV/cm, 0.1 mV/cm, 0.25 mV/cm, 0.5 mV/cm, 1 mV/cm, 2.5 mV/cm, 5 mV/cm, 10 mV/cm and 20 mV/cm. Additionally, with the Millivolts per centimeter option 66, the user may also depress the gain button to display a screen with the gain factors for auxiliary calibration factors of 10 mV/cm, 25 mV/cm, 50 mV/cm, 100 mV/cm, 250 mV/cm, 500 mV/cm and 1000 mV/cm for the auxiliary channels as well as a new maximum pressure scale for the pressure channels of 30 mm/Hg, 150 mm/Hg or 300 mm/Hg.

FIG. 12 G shows the option to select user defined high and/or low pass filters for the modified amplification system 10. As shown in FIG. 10, this screen is a selection from the filter popup screen which is likewise selected from the signals screen. The standard selections for the high pass filter are shown as 0.05 Hz, 0.5 Hz, 1.0 Hz, 10 Hz and 30 Hz. The standard selections for the low pass filter are shown as 20 Hz, 40 Hz, 100 Hz, 200 Hz and 400 Hz. Standard selections for the notch filter are shown as on or off and either 50 Hz or 60 Hz. In contrast to the amplification described above and shown in FIGS. 1–9, the present modified amplification system 10 provides the user with the ability to select one of the standard selections for the high and low pass filters or to define their high and/or low pass filters as desired for the particular study, operating environment or patient.

FIG. 12 H illustrates the Display Screen 54 which is one of the three directly accessible primary screens for the modified amplification system 10. As shown in FIG. 12 H, the Display screen 54 provides the user with the options to turn the selection of the various channels on or off and to change channel color or location as well as providing direct access to the catheter and signal screens.

As described briefly above, a primary function of the real time display monitor 70 will be to display up to 32 analog channels produced by the modified amplification system 10 in real time on a high resolution video monitor. The real time display monitor 70 preferably implements two display systems: the scrolling or panning display system and the static display system. The panning system is used to scroll up to 32 signal waveforms across the real time display monitor. The static display system does not scroll and is displayed concurrently with panning system and is used to store non-signal data such as channel labels. The preferred design of the real time display monitor of the present invention is such that the data displayed in the panning system will overlay the data displayed in the static system although, the design of the present system is such that the data from the static system may overlay the data from the panning system. Because paper copies via a chart recorder are commonly required in many institutions as a backup to the recording system of the data management and analysis system, the chart recorder may be provided as an optional component to the real time display monitor. The chart recorder operates independently from the real time display monitor and includes the same default values as the real time display monitor 70. The independent operation of the chart recorder permits a different waveform set to be recorded than that displayed on the video display.

Figure 13:
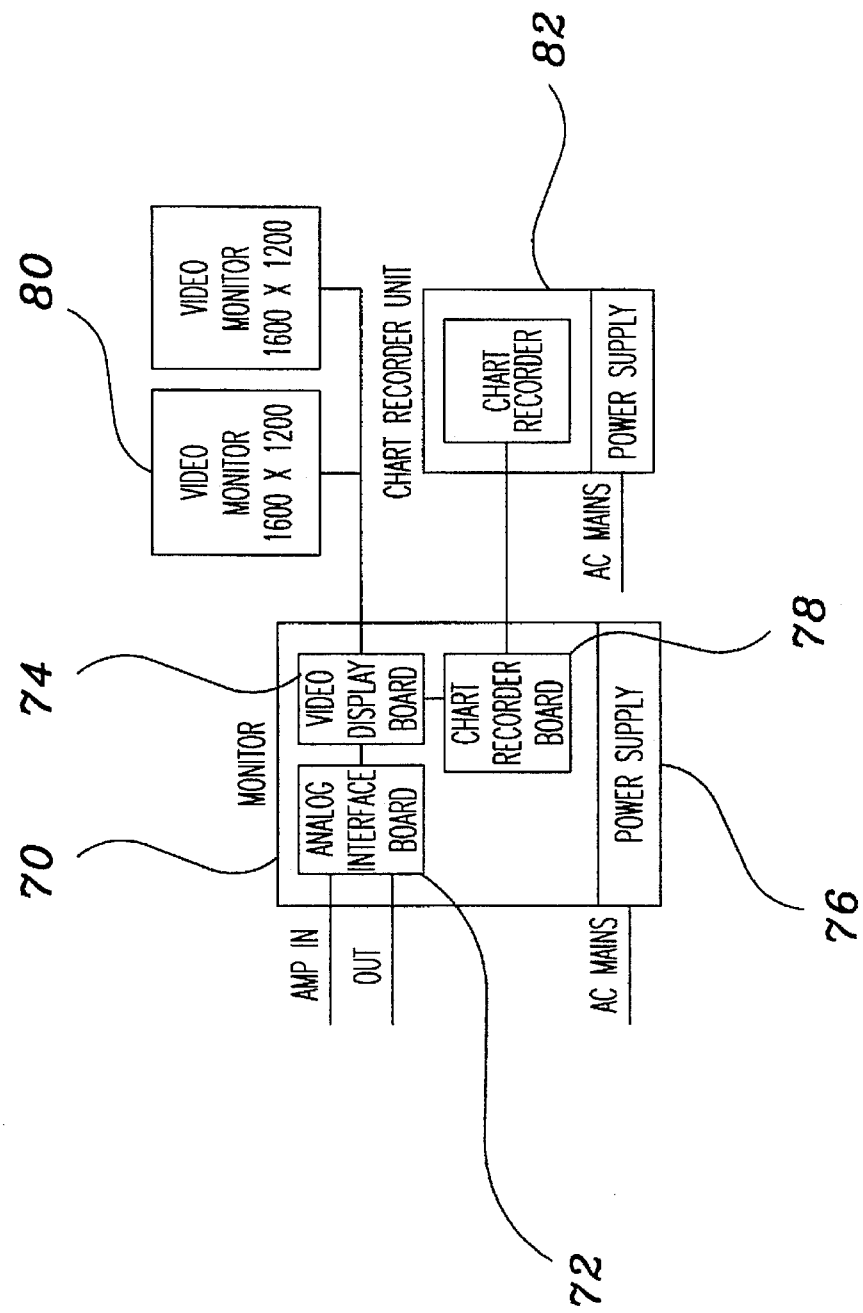
FIG. 13 is a block diagram showing the system components for the real time display monitor for the alternate preferred embodiment of the present invention.

A system block diagram of real time display monitor 70 is shown in FIG. 13. The basic components of the real time display monitor 70 broadly include an interface means or board 72 and a video display means or board 74, as well as a power supply 76 and an optional chart recorder means or board 78. As shown in FIG. 13, the real time display monitor 70 may be connected to one or more video monitors 80 through the video display board 74 and to a chart recorder 82 through the chart recorder board 78 for printing of the desired real time data. Additionally, as diagrammatically shown in FIG. 13, the real time display monitor 70 includes input and output connections to the modified amplification system 10 through the interface board 72.

Figure 14:
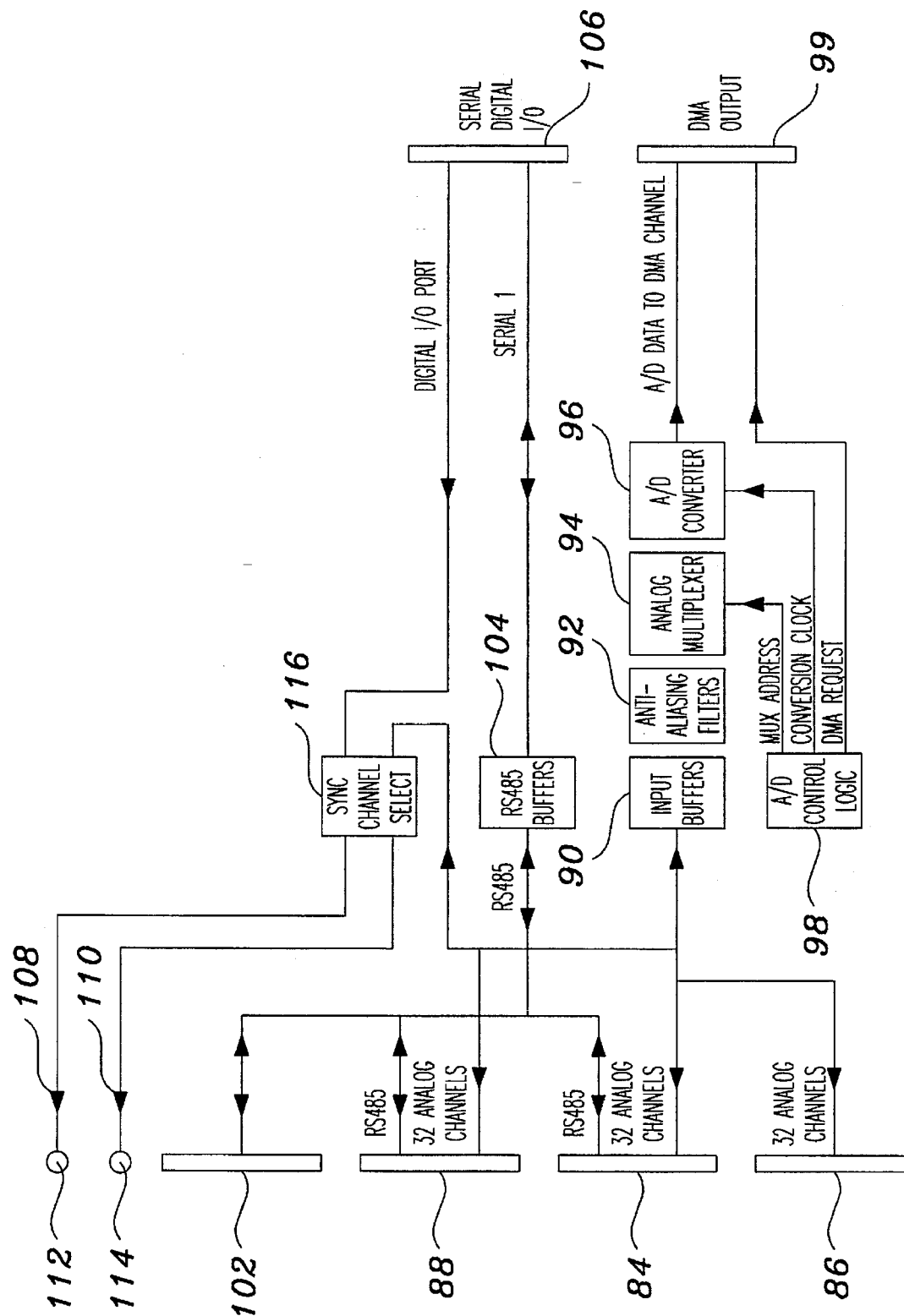
FIG. 14 is a block diagram of the interface board of the real time display monitor shown in FIG. 13.

As shown in FIG. 14, the interface board 72 of the present invention is preferably an analog interface board which receives 32 analog channels via input connector 84 from the modified amplification system 10. In a preferred form of the present invention, the input connector is preferably a 50 pin D connector with an insulation displacement connector pinout. Additionally, a connector is preferably also available as a digital data link to receive digital data for use by the modified amplification system 10. The 32 analog channels which are input through the input connector 84 are routed unbuffered to a user analog outlet 86 and a data management and analysis outlet 88. The user analog outlet 86 is preferably a 37 pin D female connector and the data management and analysis outlet is preferably a 60 pin insulated displacement connector. The 32 analog channels which are input through the input connector 84 are also buffered by operational amplifiers and buffers 90 and clamped to prevent input voltages from exceeding either amplifier power supply voltage. Each buffered input channel is then filtered to prevent aliasing by anti-aliasing filters 92 which preferably have a 3 pole Butterworth response of −1 db at 400 Hz, −3 db at 500 Hz and −18 db at 1000 Hz. The filtered input channels are then passed through an analog multiplexer 94 which multiplexes the 32 filtered input channels to a single channel to an A to D converter 96. The A to D converter 96 preferably digitizes the multiplexer output to a minimum of 12 bit resolution (4096 levels) with a full scale range of about +/−2.5 Volts and a sampling rate of a maximum of 2000 samples per second per channel. The A to D converter 96 is a conventional device having control logic 98 which is implemented in a programmable gate array or similar device. The control logic 98 provides a conversion clock to the A to D converter 96 that can be set with a minimum resolution of 8 Hz., a sequencing address to the analog multiplexer 94 and a DMA request clock as shown. The digitized data from the A to D converter 96 and the DMA request from the A to D control logic system 98 are output to a DMA output 99 which is connected to a DMA input 160 on the video display board 74.

A communication bus 100 which is preferably a half duplex RS485 communication bus is connected to the input channel 84, the data management and analysis outlet 88 and an auxiliary communication outlet 102. The communication bus 100 is also connected to the RS485 buffers and to a digital logic family such as a transistor transistor logic (TTL) receiver 104. The output of the receiver 104 is connected to a serial digital I/O port 106. The communication bus 104 is also connected to a TTL to an RS485 transmitter and the input of the transmitter is connected to the serial digital I/O port 106. The transmitter drive output is enabled by a TTL control signal which is input from the serial digital I/O port 106.

The output of the interface board 72 also includes two synchronization channels, 108 and 110, which are in communication with outlet connectors 112 and 114. Each synchronization channel, 108 or 110, is selectable from any of the 32 unbuffered input channels which are input to the interface board 72 through the input channel 84. The synchronization channel, 108 or 110, is selected by a synchronization channel selector 116 through the digital port input from the video display board 74 and the serial digital I/O port 106. The gain of both synchronization channel outputs, 108 and 110, is preferably unity.

Figure 15:
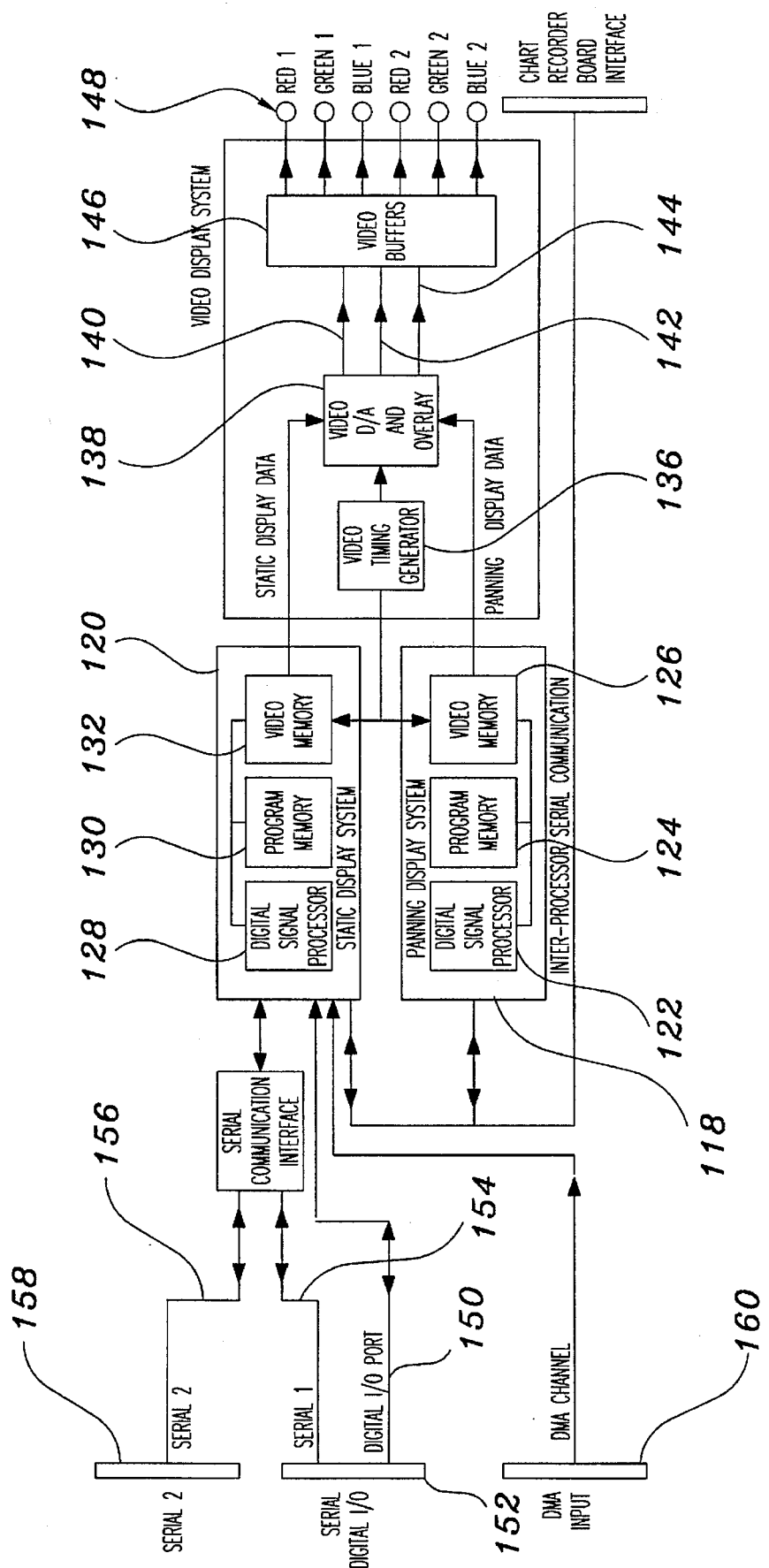
FIG. 15 is a block diagram of the video display board of the real time display monitor shown in FIG. 13.

As shown in FIG. 15 and briefly described above, the video display board 74 includes a scrolling or panning display system 118 and a static display system 120. The panning display system includes a digital signal processor 122 preferably having a 32 bit floating point architecture and which is able to execute a minimum of 20 million instructions per second and 40 million floating point operations per second. Additionally, the digital signal processor 122 preferably linearly addresses 16 million words of program and data has a minimum of one direct memory access to transfer a minimum of 128,000 words per second to the program memory. Additionally, in the preferred embodiment of the present invention, the digital signal processor will include a bi-directional serial communication interface capable of transmitting and receiving data at a minimum of 8.0 megabits per second.

The panning display system 118 also preferably includes the ability to implement two memory subsystems 124. The first memory subsystem is referred to as the static RAM and is interfaced to the digital signal processor 122 with a minimum of 128K and allows for the expansion to 256K words. The speed of the static RAM shall be sufficient to permit the digital signal processor 122 to execute with zero wait states. The other memory subsystem is referred to as the non-volatile memory. The non-volatile memory preferably includes a minimum of 128K words and is expandable to 256K words. The non-volatile memory system also retains its memory after the power to the system is removed and when power is returned, the contents of the non-volatile memory are copied to the static RAM.

Finally, the panning display system 118 also preferably includes a video memory 126 having a minimum display resolution of about 1600 horizontal pixels by 1200 vertical pixels. The video memory 126 also preferably includes a minimum of about 16 colors per pixel and an ability to permit the clearing of the display in a maximum of about 1/60 of a second.

The static display system 120 also preferably includes a digital signal processor 122 having a 32 bit floating point architecture and which is able to execute a minimum of 20 million instructions per second and 40 million floating point operations per second. Additionally, the digital signal processor 122 preferably linearly addresses 16 million words of program and data has a minimum of one direct memory access to transfer a minimum of 128,000 words per second to the program memory. Additionally, in the preferred embodiment of the present invention, the digital signal processor will include a bi-directional serial communication interface capable of transmitting and receiving data at a minimum of 8.0 megabits per second.

As with the panning display system 118 described above, the static display system 120 also preferably includes the ability to implement two memory subsystems 130. The first memory subsystem is referred to as the static RAM and is interfaced to the digital signal processor 128 with a minimum of 128K and allows for the expansion to 256K words. The speed of the static RAM shall be sufficient to permit the digital signal processor 128 to execute with zero wait states. The other memory subsystem is referred to as the non-volatile memory. The non-volatile memory preferably includes a minimum of 128K words and is expandable to 256K words. The non-volatile memory system also retains its memory after the power to the system is removed and when power is returned, the contents of the non-volatile memory are copied to the static RAM.

Finally, the static display system 120 also preferably includes a video memory 132 having a minimum display resolution of about 1600 horizontal pixels by 1200 vertical pixels. The video memory 132 also preferably includes a minimum of about 16 colors per pixel and an ability to permit the clearing of the display in a maximum of about 1/60 of a second.

As shown in FIG. 15, the video display board 74 also preferably includes a video display system 134 having a video timing generator 136 having flexible video timing control to permit various monitors and resolutions to be selected. The flexibility preferably includes the horizontal sync width, the horizontal back porch, the horizontal front porch, the horizontal active period, the vertical sync width, the vertical back porch, the vertical front porch and the vertical active period.

The video display system 134 also includes a video digital to analog converter (DAC) 138 having inputs for the input from the static display system 120 and the panning display system 118. The video DAC 138 will also preferably permit the input from the panning display system 118 to overlay the input from the static display system 120. Alternately, the video DAC 138 will permit the input from the static display system 120 to overlay the input from the panning display system 118. The preferred video DAC 138 will also provide a minimum of 16 color palettes for the input from the static display system and the panning display system 118 and will output separate Red, Green and Blue (RGB) video signals, 140, 142 and 144, which are RS-343A compatible video signals. The RGB video signals 140, 142 and 144, are output by the video DAC 138 to a video buffer 146. The buffered video signals are the passed to a plurality of RGB outputs 148 which are capable of driving the RGB signals a minimum of 100 feet (30 m) to a monitor terminated by a 75 ohm connector at its RGB inputs.

As shown in FIG. 15, the video display board 74 also includes a 16 bit digital I/O port 150 which is preferably buffered and is output to a serial digital I/O port 152. The bus input and output cycles of the digital I/O port 152 are generated by the digital signal processor 128 of the static display system 120 and includes at least 32 addressable input and output ports. The devices controlled by this I/O bus are preferably capable of extending and reducing input or output cycle times through the digital signal processor 128. The video display board 74 also preferably provides two RS232 serial communication channels referred to herein as Serial 1 (154) and Serial 2 (156).

The Serial 1 signals 154 are connected at transistor transistor logic levels to the serial digital I/O port 152. The Serial 2 signals are preferably level shifted to (or from) the RS232C levels and connected to serial port 158. The minimum baud rate for the serial 1 and serial 2 signals are preferably about 19,200 baud and about 115,200 baud as a maximum baud rate.

Figure 16:
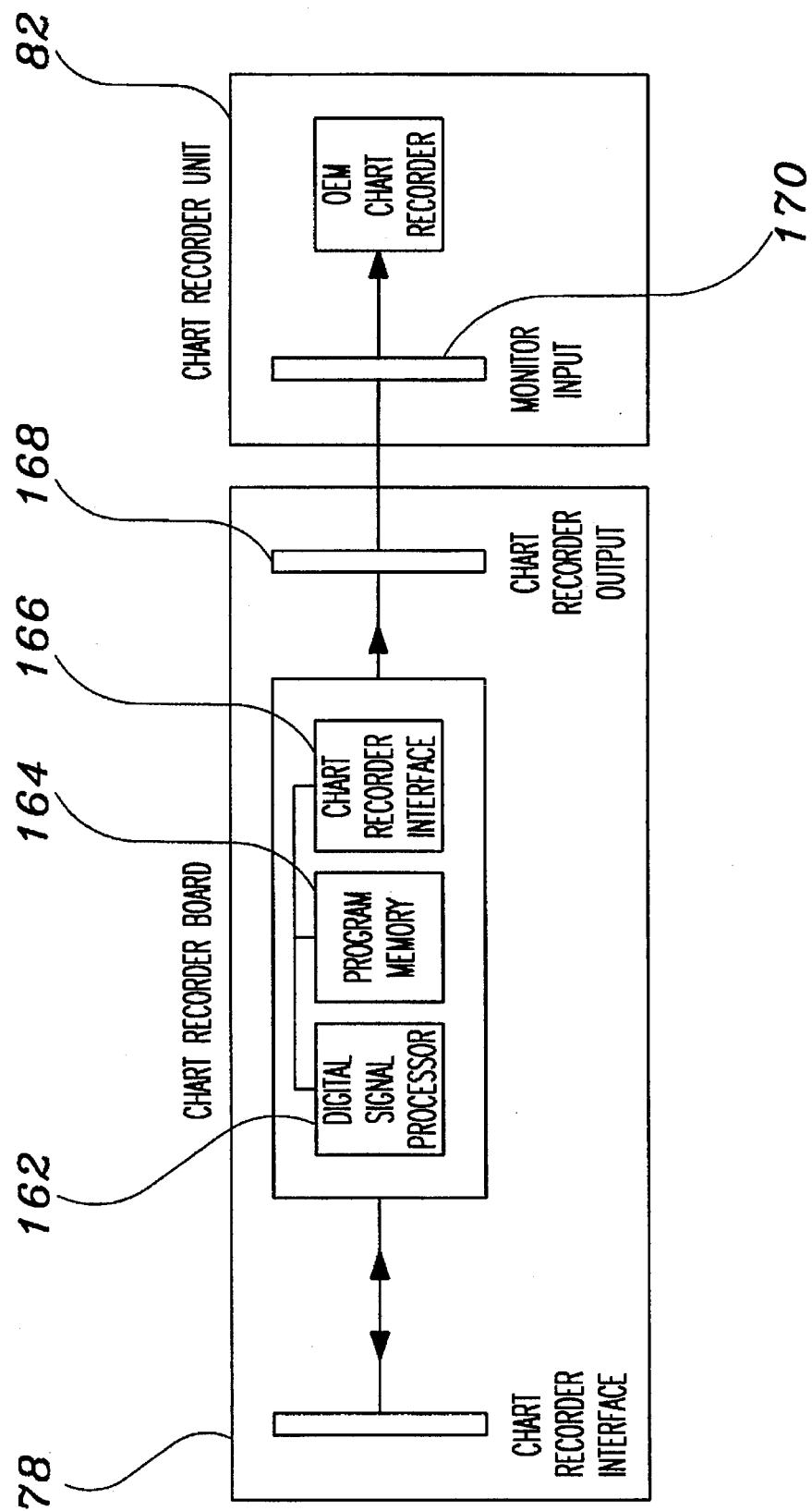
FIG. 16 is a block diagram of the chart recorder board of the real time display monitor shown in FIG. 13 and the chart recorder unit.

The real time display monitor 70 may include a chart recorder board 78 which is connected to a chart recorder 82 as shown in FIGS. 13 and 16 for printing of the wave forms and patient data. The chart recorder board 78 is insertable into the real time display monitor 70 and includes a digital signal processor 162 preferably having a 32 bit floating point architecture and which is able to execute a minimum of 20 million instructions per second and 40 million floating point operations per second. Additionally, the digital signal processor 162 preferably linearly addresses 16 million words of program and data has a minimum of one direct memory access to transfer a minimum of 128,000 words per second to the program memory. Additionally, in the preferred embodiment of the present invention, the digital signal processor 162 will include a bi-directional serial communication interface capable of transmitting and receiving data at a minimum of 8.0 megabits per second.

As with the panning display system 118 and the static display system 120 described above, the chart recorder board 78 also preferably includes the ability to implement two memory subsystems 164. The first memory subsystem is referred to as the static RAM and is interfaced to the digital signal processor 162 with a minimum of 128K and allows for the expansion to 256K words. The speed of the static RAM shall be sufficient to permit the digital signal processor 162 to execute with zero wait states. The other memory subsystem is referred to as the non-volatile memory. The non-volatile memory preferably includes a minimum of 128K words and is expandable to 256K words. The non-volatile memory system also retains its memory after the power to the system is removed and when power is returned, the contents of the non-volatile memory are copied to the static RAM.

The chart recorder 82 communicates with the real time display monitor 70 through the chart recorder interface 166 and chart recorder output 168 of the real time display monitor and a real time display monitor input 170 on the chart recorder 82. As discussed above, the chart recorder 82 is preferably a conventional chart recorder which includes a 16 bit digital interface and has an adjustable paper speed and the resolution of the chart recorder 82 is at least 8 dots/mm and will vary with the paper speed.

Figure 17:
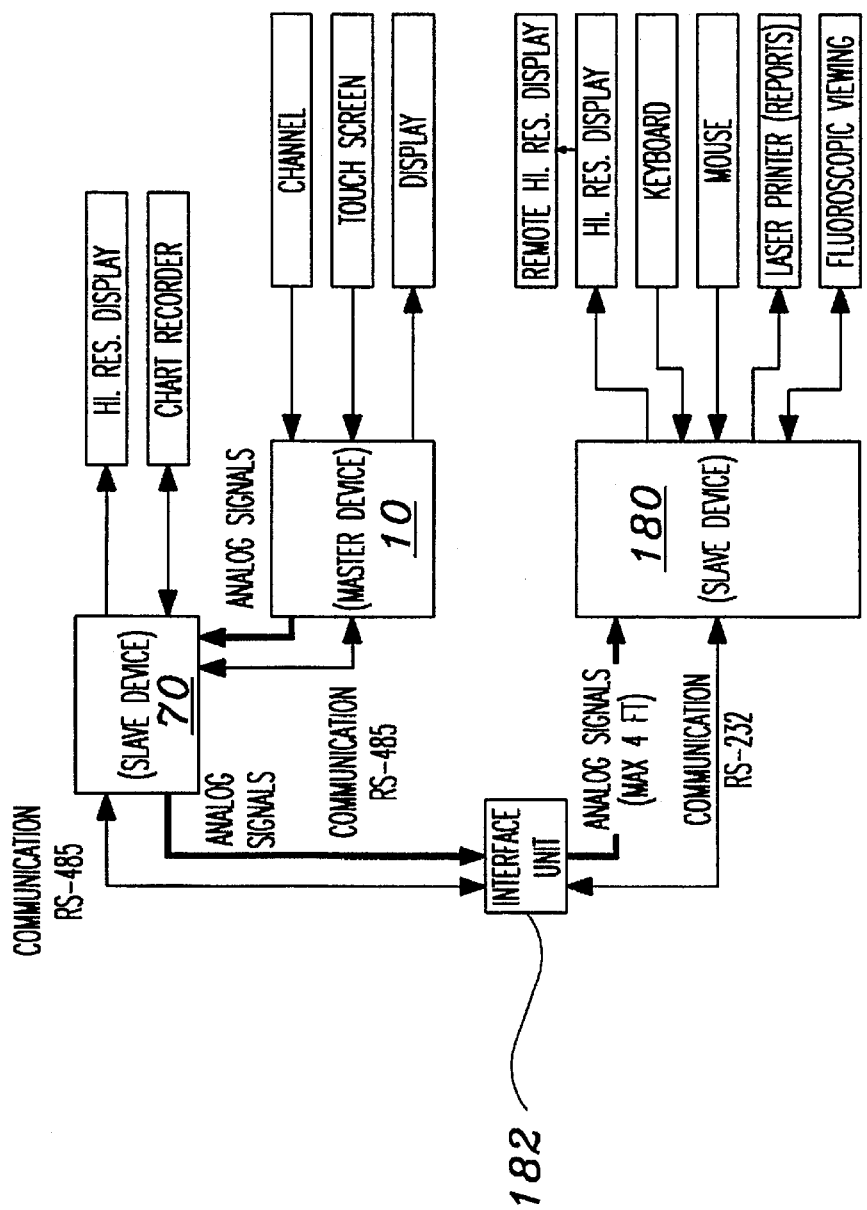
FIGS. 17 and 18 are block diagrams of the component and functional configurations of one form of the present invention.
Figure 18:
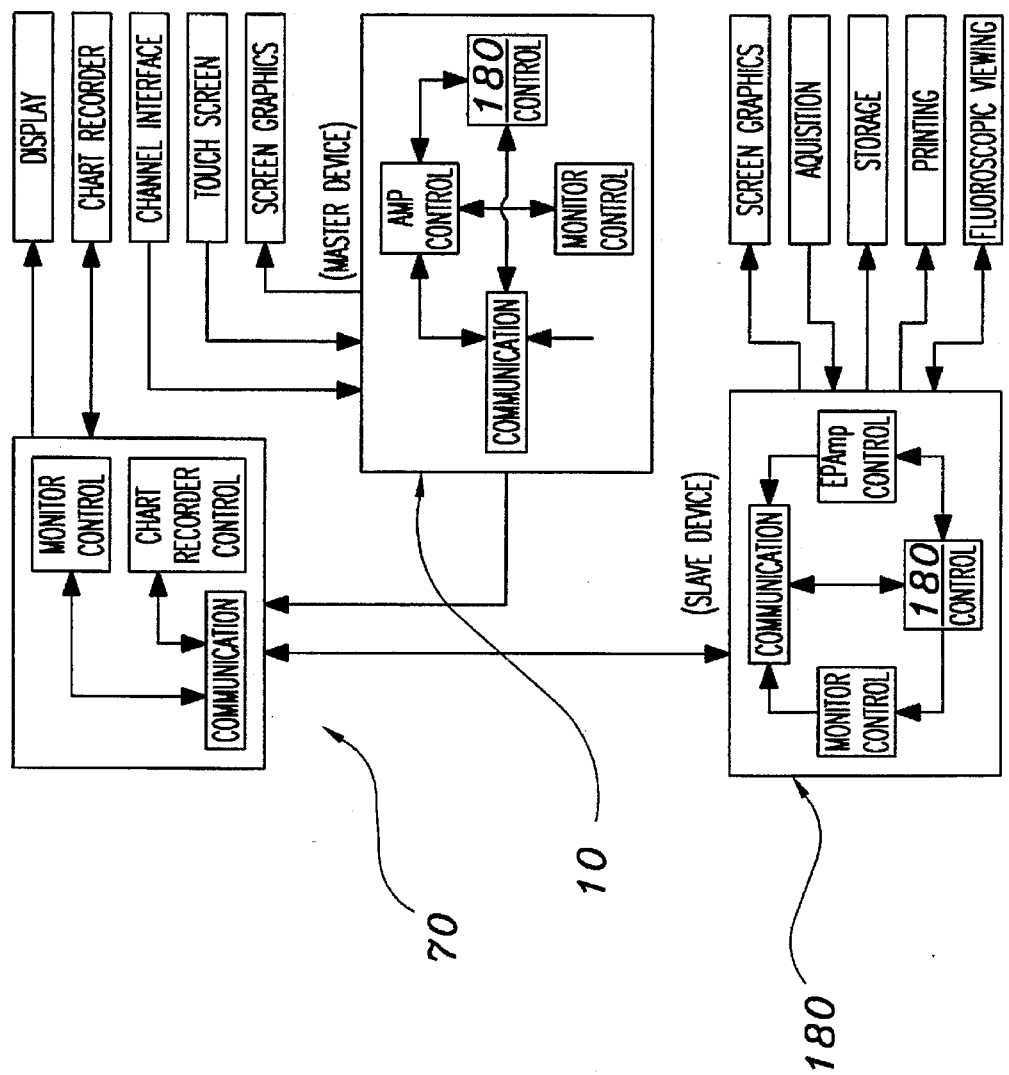
Figure 19:
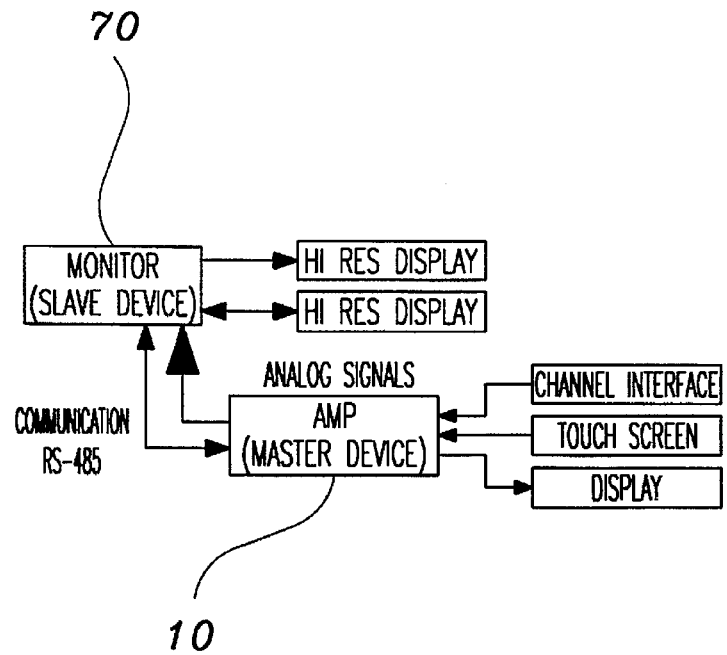
FIG. 19 is a block diagram of an alternate component configuration of the present invention.

FIGS. 17 to 19 are illustrative of two electrophysiology equipment configurations which may be used to perform a particular study. As discussed in detail above, the modified amplification system 10 and the real time display monitor 70 of the present invention form an integral part of a versatile electrophysiology system. The modified amplification system 10 and the real time display monitor 70 as described above allow for the use of the modified amplification system 10 as a master device in various configurations to control the operation of the real time display monitor 70, video monitors 80, chart recorder 82 and the data management and analysis system 180 from the modified amplification system 10. The configuration of the system shown in FIG. 19 is particularly useful in hospital situations where there is limited space or where all of the capabilities of the particular unit are not necessary to perform and monitor the desired procedure.

As discussed above, the data management and analysis system 180 preferably provides up to 32 channels of real time analog waveform acquisition data with a variety of display options and storage and statistical capabilities. Once storage of the data and wave forms has been performed, playback, markers, annotations, analysis and hard copy printouts may be processed. As shown in FIG. 17, the data management and analysis system 180 may be used as a slave device to the modified amplification system 10 which functions as a master device in the configuration shown. In this configuration, the data management and analysis system 180, the real time display monitor 70 and the modified amplification system 10 include a commercially available poll response communications protocol. This communications protocol is used in the master device to initiate and maintain the communications with the slave devices while the slave devices use this communications protocol to respond to communications from the master device.

The interface unit 182 translates the RS-232 serial communications of the data management and analysis system 180 to the RS-485 serial communications used by the modified amplification system 10 and also multiplexes 32 channels of input data from the modified amplification system 10 to 2 times 16 channels of data which may be used in the data management and analysis system 180.

FIGS. 17 and 18 illustrate the hardware and functional layouts of one of the configurations available with the present invention where the user is able to perform all of the features and functions of a complete electrophysiology system. As shown in FIG. 17, the modified amplification system 10 functions as the master control system which communicates with the real time display monitor 70 via an RS-485 interface and also sends analog signals to the real time display monitor 70. The real time display monitor 70 communicates with the interface unit 182 via an RS-485 interface and also sends 32 channels of analog data signals to the interface unit 182. The interface unit 182 communicates with the data management and analysis unit 180 through an RS-232 interface and sends 2 times 16 analog data signals to the data management and analysis unit 180. FIG. 18 illustrates the functional diagram of the configuration shown in FIG. 17. Various exemplary capabilities of the configurations shown in FIGS. 17 and 18 are shown in association with the appropriate components.

FIG. 19 illustrates a modified version of an electrophysiology system which is designed to be portable and provides the display and printing capabilities described above in conjunction with the discussions relating to the modified amplification system 10 and the real time display monitor 70. As shown in FIG. 19, the modified amplification system 10 communicates with the real time display monitor 70 through as RS-485 interface and 32 channel analog data signals are sent from the modified amplification system 10 to the real time display monitor 70. Various exemplary capabilities of the configuration shown in FIG. 19 are shown in association with the appropriate components.

Figure 20:
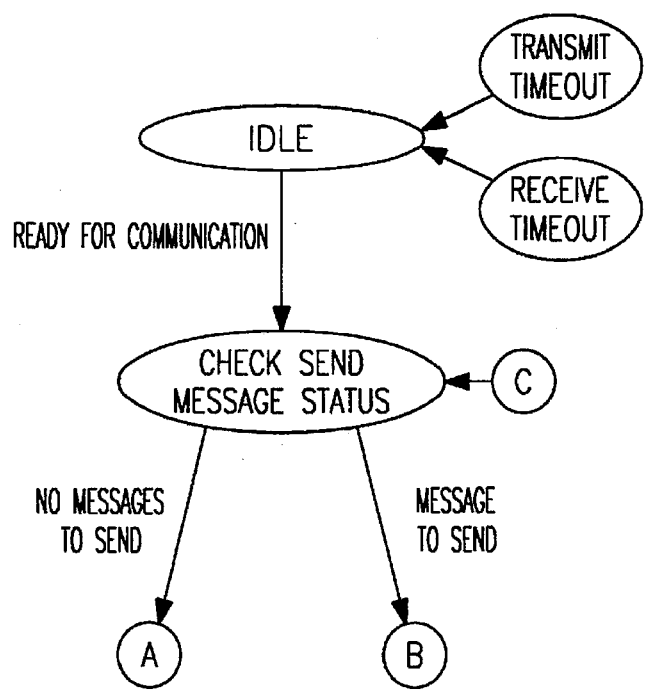
FIGS. 20–22 are flow communication diagrams showing the communications for system configurations of the type shown in FIG. 17–19 wherein the modified integrated electrical signal switching and amplifying system is the master device.
Figure 21:
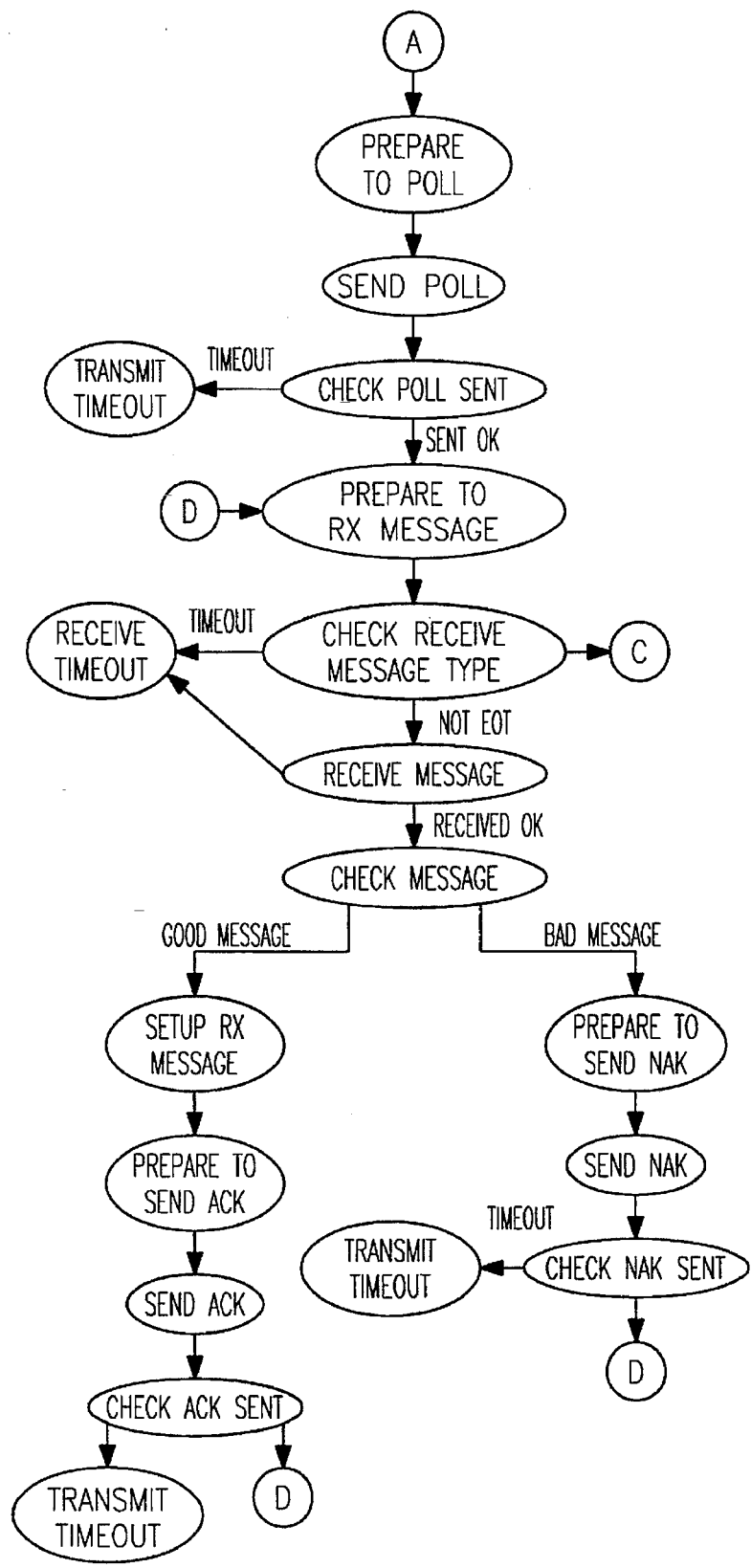
Figure 22:
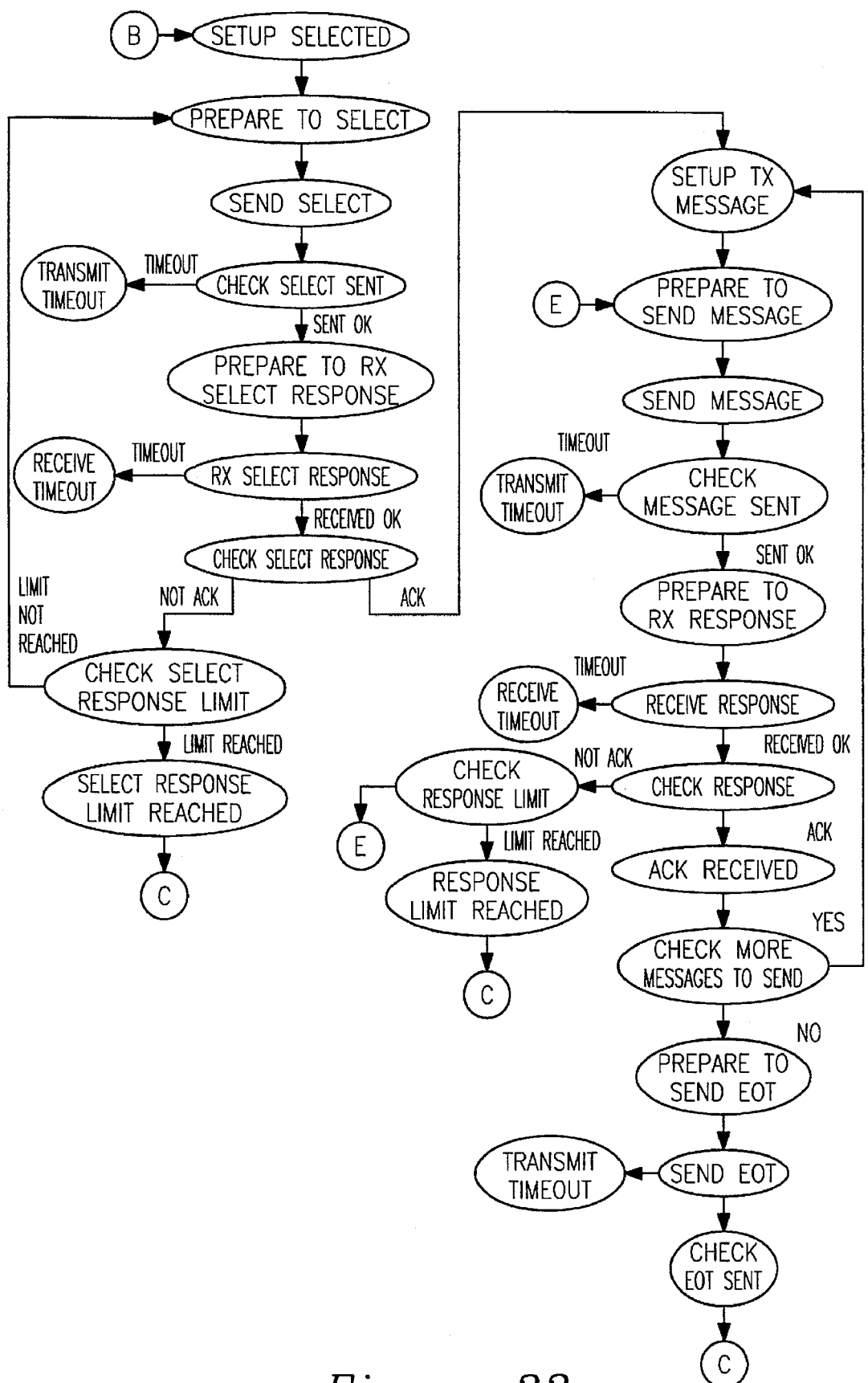

FIGS. 20–22 are illustrative of the preferred form of the communication flow between the modified amplification system 10 and the real time display monitor 70 and the data management and analysis system 180 where the modified amplification system 10 is the master device and the real time display monitor 70 and the data management and analysis system 180 are the slave devices. As shown in the drawings, the communications are initiated and controlled by the modified amplification system 10.

It will be apparent from the foregoing that, while particular embodiments of the invention have been illustrated and described, various modifications can be made thereto without departing from the spirit and scope of the invention. Accordingly, it is not intended that the invention be limited, except as by the appended claims.

What is claimed is:

1. An electrophysiology monitoring system for monitoring the physiological data of a patient from an electrophysiology study, the system comprising an amplification system for receiving and amplifying physiological data from a patient during an electrophysiology study;

said amplification system including a physiological data receiver for receiving the physiological data from a patient;

a physiological data amplifier for receiving the received physiological data and amplifying the physiological data;

an analog to digital converter for receiving the amplified physiological data and converting the amplified physiological data into digital physiological data;

a digital signal processor for receiving the digital physiological data and performing a signal switching operation on the digital physiological data;

a physiological data output for outputting the switched physiological data from said amplification system; and a real time monitor display system for displaying the switched physiological data received from said amplification system wherein the display of the switched physiological data on said display system is controlled by command signals transmitted from said amplification system to said display system.

2. The system of claim 1 wherein said monitoring system further includes a data management system in operative communication with said amplification system and said display system is alternately controllable by said amplification system and said data management system upon receipt of said command signals from said amplification system.

3. The system of claim 1 wherein said display system includes a monitor including a triggered sweep mode which overlays current physiological data on previously displayed physiological data on said monitor.

4. The system of claim 1 including a chart recorder for printing physiological data and said display system including a display monitor wherein said chart recorder and said display monitor are independently configurable upon receipt of communications from said amplification system.

5. The system of claim 1 further including a separate data management system having a microprocessor therein which is in communication with and receives said command signals from said amplification system and said display system includes a real time display monitor operatively associated therewith and the operation of said monitor and said data management system is in response to said command signals received from said amplification system.

6. The system of claim 1 further including a separate chart recorder operatively connected thereto and including a receiver therein to receive said command signals from said amplification system and said display system includes a real time display monitor operatively associated therewith and the operation of said monitor and said chart recorder being in response to said command signals received from said amplification system.

7. The system of claim 6 further including said amplification system generating separate command signals from said amplification system for receipt by said chart recorder and said display system to enable the independent operation of said chart recorder and said display system.

8. An electrophysiology monitoring system for monitoring the physiological data of a patient from an electrophysiology study, said monitoring system including an amplification system for receiving and amplifying physiological signals from the body of the patient during an electrophysiology study;

said amplification system including a physiological signal receiver for receiving the physiological signals from a patient;

a physiological signal amplifier for receiving the received physiological signals and amplifying the physiological signals;

an analog to digital converter for receiving the amplified physiological signals and converting the amplified physiological signals into digital physiological signals;

a digital signal processor for receiving the digital physiological signals and performing a signal switching operation on the digital physiological signals;

a physiological signal output for outputting the switched physiological signals from said amplification system and said switched physiological signals are representative of the physiological signals received from a patient;

said amplification system further including means for generating control signals for transmission to said display system;

a display system in operative communication with said display system including, an interface means for interfacing with said switched physiological signals received from said amplification system; and a video display means for outputting said switched physiological signals from said interface means to a means for displaying the switched physiological signals in response to receipt of said control signals from said amplification system and wherein said display means includes a means static display of said switched physiological signals and a means for panning display of said switched physiological signals therein.

9. The system of claim 8 wherein the output of said means for static display of said switched physiological signals overlays the output of said means for panning display of said switched physiological signals on said means for displaying the switched physiological signals.

10. The system of claim 8 wherein the output of said means for panning display overlays the output of said means for static display on said means for displaying switched physiological signals.

11. The system of claim 8 wherein said means for displaying the switched physiological signals of said video display means includes a real time display monitor and a chart recorder for the display and printing of the switched physiological signals.

12. The system of claim 8 wherein said amplification system includes user settable filters therein to apply high and low pass filters to said digital physiological signals.

13. The system of claim 12 wherein said amplification system includes notch filters therein which are selectable to filter selected portions of said digital physiological signals.

14. A method of performing the monitoring of physiological signals from a patient during an electrophysiology study using an electrophysiology monitoring system which includes an amplification system having a display screen thereon and a display system controlled by the amplification system, the method including the steps of;

receiving a physiological signal from the patient with a receiver from the amplification system;

amplifying the physiological signal received by the receiver with an amplifier to create an amplified signal;

converting the amplified signal received from the amplifier with an analog to digital converter to create a digital physiological signal;

performing a switching operation on the digital physiological signal received from the converter with a digital signal processor to create a switched digital physiological signal;

outputting the switched physiological signal from the amplification system; and actuating a portion of the display screen on the amplification system to select settings for the application of high and low pass filters to the digital physiological signal in the amplification system.

15. A method of performing the monitoring of an electrophysiology study using an electrophysiology monitoring system which includes an amplification system having a display screen thereon and a display system controlled by the amplification system, the method including the steps of;

receiving a physiological signal from the patient with a receiver from the amplification system;

amplifying the physiological signal received by the receiver with an amplifier to create an amplified signal;

converting the amplified signal received from the amplifier with an analog to digital converter to create a digital physiological signal;

performing a switching operation on the digital physiological signal received from the converter with a digital signal processor to create a switched digital physiological signal;

outputting the switched physiological signal from the amplification system;

actuating the display screen on the amplification system to access a catheters screen for performing catheter setup, grid formation, real time display or screen modes, mapping, tagging, charting or storage for the amplification system;

actuating the display screen on the amplification system to access a signals screen for selecting notch filter settings and settings for high and low pass filters, channel names, limiter settings, gain settings and channel selections; and actuating the display screen on the amplification system to access a display screen to adjust channel color and channel location and to turn selected channels on or off.

16. A method of performing the monitoring of physiological signals from a patient during an electrophysiology study using an electrophysiology monitoring system which includes an amplification system with a chart recorder and a display system controlled by the amplification system, the method including the steps of;

receiving a physiological signal from the patient with a receiver from the amplification system;

amplifying the physiological signal received by the receiver with an amplifier to create an amplified signal;

converting the amplified signal received from the amplifier with an analog to digital converter to create a digital physiological signal;

performing a switching operation on the digital physiological signal received from the converter with a digital signal processor to create a switched digital physiological signal;

outputting the switched physiological signal from the amplification system; and generating a control signal in the amplification system for transmission to the chart recorder and display system to enable the amplification system to control the operation of the chart recorder and display system.

17. The method of claim 16 wherein a plurality of control signals are generated by the amplification system to separately control the operation of the chart recorder and the display system.

* * * * *

UNITED STATES PATENT AND TRADEMARK OFFICE
CERTIFICATE OF CORRECTION

PATENT NO. : 5,640,967
DATED : June 24, 1997
INVENTOR(S) : Fine et al.

It is certified that error appears in the above-indentified patent and that said Letters Patent is hereby corrected as shown below:

In column 25 line 63 after "means" insert "for"

Signed and Sealed this

Twenty-eighth Day of October, 1997

Attest:

BRUCE LEHMAN

Attesting Officer

Commissioner of Patents and Trademarks